(12) United States Patent
Bharadwaj et al.

(10) Patent No.: US 9,694,361 B2
(45) Date of Patent: Jul. 4, 2017

(54) FLUIDIC DEVICES, SYSTEMS, AND METHODS FOR ENCAPSULATING AND PARTITIONING REAGENTS, AND APPLICATIONS OF SAME

(71) Applicant: 10X Genomics, Inc., Pleasanton, CA (US)

(72) Inventors: Rajiv Bharadwaj, Pleasanton, CA (US); Kevin Ness, Pleasanton, CA (US); Debkishore Mitra, Berkeley, CA (US); Donald Masquelier, Tracy, CA (US); Anthony Makarewicz, Livermore, CA (US); Christopher Hindson, Pleasanton, CA (US); Benjamin Hindson, Pleasanton, CA (US); Serge Saxonov, Oakland, CA (US)

(73) Assignee: 10X Genomics, Inc., Pleasanton, CA (US)

(*) Notice: Subject to any disclaimer, the term of this patent is extended or adjusted under 35 U.S.C. 154(b) by 0 days.

(21) Appl. No.: 14/682,952

(22) Filed: Apr. 9, 2015

(65) Prior Publication Data
US 2015/0292988 A1 Oct. 15, 2015

Related U.S. Application Data

(60) Provisional application No. 61/977,804, filed on Apr. 10, 2014.

(51) Int. Cl.
| | | |
|---|---|---|
| *B01L 3/00* | (2006.01) | |
| *G01N 15/06* | (2006.01) | |
| *C12M 3/00* | (2006.01) | |
| *B01F 3/00* | (2006.01) | |
| *B01F 3/04* | (2006.01) | |
| *B01L 3/02* | (2006.01) | |
| *G01N 35/08* | (2006.01) | |
| *G01N 35/00* | (2006.01) | |
| *G01N 35/10* | (2006.01) | |

(52) U.S. Cl.
CPC ....... *B01L 3/502761* (2013.01); *B01L 3/0241* (2013.01); *B01L 3/502784* (2013.01); *B01L 2200/0673* (2013.01); *B01L 2300/0816* (2013.01); *B01L 2400/049* (2013.01); *B01L 2400/086* (2013.01); *G01N 35/085* (2013.01); *G01N 2035/00237* (2013.01); *G01N 2035/1034* (2013.01)

(58) Field of Classification Search
CPC . C12Q 1/68; C12M 1/00; B01L 3/0241; B01J 13/00; C40B 50/06
USPC ......... 422/68.1, 502; 435/6.8, 283.1, 288.5; 516/7, 9
See application file for complete search history.

(56) References Cited

U.S. PATENT DOCUMENTS

| | | |
|---|---|---|
| 4,582,802 A | 4/1986 | Zimmerman et al. |
| 5,149,625 A | 9/1992 | Church et al. |
| 5,202,231 A | 4/1993 | Drmanac et al. |
| 5,413,924 A | 5/1995 | Kozak et al. |
| 5,436,130 A | 7/1995 | Mathies et al. |
| 5,512,131 A | 4/1996 | Kumar et al. |
| 5,587,128 A | 12/1996 | Wilding et al. |
| 5,605,793 A | 2/1997 | Stemmer |
| 5,618,711 A | 4/1997 | Gelfand et al. |
| 5,658,548 A | 8/1997 | Padhye et al. |
| 5,695,940 A | 12/1997 | Drmanac et al. |
| 5,736,330 A | 4/1998 | Fulton |
| 5,756,334 A | 5/1998 | Perler et al. |
| 5,834,197 A | 11/1998 | Parton |
| 5,851,769 A | 12/1998 | Gray et al. |
| 5,856,174 A | 1/1999 | Lipshutz et al. |
| 5,958,703 A | 9/1999 | Dower et al. |
| 5,994,056 A | 11/1999 | Higuchi |
| 6,046,003 A | 4/2000 | Mandecki |
| 6,051,377 A | 4/2000 | Mandecki |
| 6,057,107 A | 5/2000 | Fulton |
| 6,103,537 A | 8/2000 | Ullman et al. |
| 6,133,436 A | 10/2000 | Koester et al. |
| 6,143,496 A | 11/2000 | Brown et al. |
| 6,172,218 B1 | 1/2001 | Brenner |
| 6,265,552 B1 | 7/2001 | Schatz |
| 6,297,006 B1 | 10/2001 | Drmanac et al. |
| 6,297,017 B1 | 10/2001 | Schmidt et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,406,848 B1 | 6/2002 | Bridgham et al. |

(Continued)

FOREIGN PATENT DOCUMENTS

| | | |
|---|---|---|
| EP | 0249007 A2 | 12/1987 |
| EP | 0271281 A2 | 6/1988 |

(Continued)

OTHER PUBLICATIONS

U.S. Appl. No. 14/624,468, filed Feb. 17, 2015, Hindson et al.

(Continued)

*Primary Examiner* — Narayan Bhat
(74) *Attorney, Agent, or Firm* — Wilson Sonsini Goodrich & Rosati

(57) ABSTRACT

The disclosure provides devices, systems and methods for the generation of encapsulated reagents and the partitioning of encapsulated reagents for use in subsequent analyses and/or processing, such as in the field of biological analyses and characterization.

25 Claims, 10 Drawing Sheets

(56) References Cited

U.S. PATENT DOCUMENTS

| | | |
|---|---|---|
| 6,432,360 B1 | 8/2002 | Church |
| 6,485,944 B1 | 11/2002 | Church et al. |
| 6,511,803 B1 | 1/2003 | Church et al. |
| 6,524,456 B1 | 2/2003 | Ramsey et al. |
| 6,586,176 B1 | 7/2003 | Trnovsky et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,884,788 B2 | 4/2005 | Bulpitt et al. |
| 6,913,935 B1 | 7/2005 | Thomas |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,268,167 B2 | 9/2007 | Higuchi et al. |
| 7,282,370 B2 | 10/2007 | Bridgham et al. |
| 7,297,485 B2 | 11/2007 | Bornarth et al. |
| 7,323,305 B2 | 1/2008 | Leamon et al. |
| 7,425,431 B2 | 9/2008 | Church et al. |
| 7,536,928 B2 | 5/2009 | Kazuno |
| 7,604,938 B2 | 10/2009 | Takahashi et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,708,949 B2 * | 5/2010 | Stone .................... B01F 3/0807 422/110 |
| 7,709,197 B2 | 5/2010 | Drmanac |
| 7,745,178 B2 | 6/2010 | Dong et al. |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,053,192 B2 | 11/2011 | Bignell et al. |
| 8,067,159 B2 | 11/2011 | Brown et al. |
| 8,133,719 B2 | 3/2012 | Drmanac et al. |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,304,193 B2 | 11/2012 | Ismagilov et al. |
| 8,329,407 B2 | 12/2012 | Ismagilov et al. |
| 8,592,150 B2 | 11/2013 | Drmanac et al. |
| 8,603,749 B2 | 12/2013 | Gillevet |
| 8,679,756 B1 | 3/2014 | Brenner et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagliov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,986,286 B2 | 3/2015 | Tanghoj et al. |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,249,460 B2 | 2/2016 | Pushkarev et al. |
| 9,347,059 B2 | 5/2016 | Saxonov |
| 9,388,465 B2 | 7/2016 | Hindson et al. |
| 9,410,201 B2 | 8/2016 | Hindson et al. |
| 2001/0020588 A1 | 9/2001 | Adourian et al. |
| 2001/0044109 A1 | 11/2001 | Mandecki |
| 2002/0034737 A1 | 3/2002 | Drmanac |
| 2002/0051992 A1 | 5/2002 | Bridgham et al. |
| 2002/0089100 A1 | 7/2002 | Kawasaki |
| 2002/0092767 A1 | 7/2002 | Bjornson et al. |
| 2002/0179849 A1 | 12/2002 | Maher et al. |
| 2003/0008285 A1 | 1/2003 | Fischer |
| 2003/0008323 A1 | 1/2003 | Ravkin et al. |
| 2003/0027203 A1 | 2/2003 | Fields |
| 2003/0027221 A1 | 2/2003 | Scott et al. |
| 2003/0028981 A1 | 2/2003 | Chandler et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0082587 A1 | 5/2003 | Seul et al. |
| 2003/0104466 A1 | 6/2003 | Knapp et al. |
| 2003/0108897 A1 | 6/2003 | Drmanac |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0040851 A1 | 3/2004 | Karger et al. |
| 2004/0063138 A1 | 4/2004 | McGinnis et al. |
| 2004/0132122 A1 | 7/2004 | Banerjee et al. |
| 2004/0214175 A9 | 10/2004 | McKernan et al. |
| 2004/0258701 A1 | 12/2004 | Dominowski et al. |
| 2005/0019839 A1 | 1/2005 | Jespersen et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0287572 A1 | 12/2005 | Mathies et al. |
| 2006/0002890 A1 | 1/2006 | Hersel et al. |
| 2006/0020371 A1 | 1/2006 | Ham et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0054119 A1 | 3/2007 | Garstecki et al. |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0154903 A1 | 7/2007 | Marla et al. |
| 2007/0160503 A1 | 7/2007 | Sethu et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0213766 A1 | 9/2008 | Brown et al. |
| 2008/0228268 A1 | 9/2008 | Shannon et al. |
| 2008/0241820 A1 | 10/2008 | Krutzik et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0048124 A1 | 2/2009 | Leamon et al. |
| 2009/0053169 A1 | 2/2009 | Castillo et al. |
| 2009/0068170 A1 | 3/2009 | Weitz et al. |
| 2009/0098555 A1 | 4/2009 | Roth et al. |
| 2009/0118488 A1 | 5/2009 | Drmanac et al. |
| 2009/0137404 A1 | 5/2009 | Drmanac et al. |

(56) References Cited

U.S. PATENT DOCUMENTS

| | | |
|---|---|---|
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0264299 A1 | 10/2009 | Drmanac et al. |
| 2009/0286687 A1 | 11/2009 | Dressman et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0035254 A1 | 2/2010 | Williams |
| 2010/0062494 A1 | 3/2010 | Church et al. |
| 2010/0069263 A1 | 3/2010 | Shendure et al. |
| 2010/0105112 A1 | 4/2010 | Holtze et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0187705 A1* | 7/2010 | Lee ................ B01J 13/14 264/5 |
| 2010/0210479 A1 | 8/2010 | Griffiths et al. |
| 2011/0033548 A1 | 2/2011 | Lai et al. |
| 2011/0033854 A1 | 2/2011 | Drmanac et al. |
| 2011/0053798 A1 | 3/2011 | Hindson et al. |
| 2011/0071053 A1 | 3/2011 | Drmanac et al. |
| 2011/0086780 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0217736 A1 | 9/2011 | Hindson |
| 2011/0218123 A1 | 9/2011 | Weitz et al. |
| 2011/0263457 A1 | 10/2011 | Krutzik et al. |
| 2011/0267457 A1 | 11/2011 | Weitz et al. |
| 2011/0281738 A1 | 11/2011 | Drmanac et al. |
| 2011/0305761 A1 | 12/2011 | Shum et al. |
| 2011/0319281 A1 | 12/2011 | Drmanac |
| 2012/0000777 A1 | 1/2012 | Garrell et al. |
| 2012/0010098 A1 | 1/2012 | Griffiths et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0172259 A1 | 7/2012 | Rigatti et al. |
| 2012/0190032 A1 | 7/2012 | Ness et al. |
| 2012/0190037 A1 | 7/2012 | Durin et al. |
| 2012/0196288 A1 | 8/2012 | Beer |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0309002 A1 | 12/2012 | Link |
| 2012/0316074 A1 | 12/2012 | Saxonov |
| 2013/0028812 A1 | 1/2013 | Prieto et al. |
| 2013/0046030 A1 | 2/2013 | Rotem et al. |
| 2013/0078638 A1 | 3/2013 | Berka et al. |
| 2013/0079231 A1 | 3/2013 | Pushkarev et al. |
| 2013/0109575 A1 | 5/2013 | Kleinschmidt et al. |
| 2013/0157870 A1 | 6/2013 | Pushkarev et al. |
| 2013/0157899 A1 | 6/2013 | Adler, Jr. et al. |
| 2013/0178368 A1 | 7/2013 | Griffiths et al. |
| 2013/0189700 A1 | 7/2013 | So et al. |
| 2013/0203675 A1 | 8/2013 | Desimone et al. |
| 2013/0210639 A1 | 8/2013 | Link et al. |
| 2013/0210991 A1 | 8/2013 | Fonnum et al. |
| 2013/0211055 A1 | 8/2013 | Raines et al. |
| 2013/0225418 A1 | 8/2013 | Watson |
| 2013/0274117 A1 | 10/2013 | Church et al. |
| 2013/0296173 A1 | 11/2013 | Callow et al. |
| 2013/0343317 A1 | 12/2013 | Etemad et al. |
| 2014/0037514 A1 | 2/2014 | Stone et al. |
| 2014/0057799 A1 | 2/2014 | Johnson et al. |
| 2014/0065234 A1 | 3/2014 | Shum et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0206554 A1 | 7/2014 | Hindson et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0287963 A1 | 9/2014 | Hindson et al. |
| 2014/0302503 A1 | 10/2014 | Lowe et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov |
| 2015/0111256 A1 | 4/2015 | Church et al. |
| 2015/0119280 A1 | 4/2015 | Srinivas et al. |
| 2015/0218633 A1 | 8/2015 | Hindson et al. |
| 2015/0224466 A1 | 8/2015 | Hindson et al. |
| 2015/0225777 A1 | 8/2015 | Hindson et al. |
| 2015/0225778 A1 | 8/2015 | Hindson et al. |
| 2015/0298091 A1 | 10/2015 | Weitz et al. |
| 2015/0299772 A1 | 10/2015 | Zhang |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0024558 A1 | 1/2016 | Hardenbol et al. |
| 2016/0122817 A1 | 5/2016 | Jarosz et al. |
| 2016/0244742 A1 | 8/2016 | Linnarsson et al. |
| 2016/0244809 A1 | 8/2016 | Belgrader et al. |
| 2016/0257984 A1 | 9/2016 | Hardenbol et al. |
| 2016/0304860 A1 | 10/2016 | Hindson et al. |

FOREIGN PATENT DOCUMENTS

| | | | |
|---|---|---|---|
| EP | | 0637996 B1 | 7/1997 |
| EP | | 1019496 B1 | 9/2004 |
| EP | | 1482036 B1 | 10/2007 |
| EP | | 1594980 B1 | 11/2009 |
| EP | | 1967592 B1 | 4/2010 |
| EP | | 2258846 A2 | 12/2010 |
| EP | | 2145955 B1 | 2/2012 |
| EP | | 1905828 B1 | 8/2012 |
| EP | | 2136786 B1 | 10/2012 |
| EP | | 1908832 B1 | 12/2012 |
| EP | | 2540389 A1 | 1/2013 |
| EP | | 2752664 A1 | 7/2014 |
| GB | | 2485850 A | 5/2012 |
| GB | WO 2014/053854 | | * 4/2014 |
| JP | | S 5949832 A | 3/1984 |
| JP | | 2006-507921 A | 3/2006 |
| JP | | 2006-289250 A | 10/2006 |
| JP | | 2007-268350 A | 10/2007 |
| JP | | 2009-208074 A | 9/2009 |
| WO | WO-9530782 A1 | | 11/1995 |
| WO | WO 96/29629 A2 | | 3/1996 |
| WO | WO 96/41011 A1 | | 12/1996 |
| WO | WO 99/09217 A1 | | 2/1999 |
| WO | WO 99/52708 A1 | | 10/1999 |
| WO | WO 00/08212 A1 | | 2/2000 |
| WO | WO 00/26412 A1 | | 5/2000 |
| WO | WO-0070095 A2 | | 11/2000 |
| WO | WO 01/14589 A2 | | 3/2001 |
| WO | WO 02/31203 A2 | | 10/2001 |
| WO | WO 01/89787 A2 | | 11/2001 |
| WO | WO 02/086148 A1 | | 10/2002 |
| WO | WO 2004/002627 A2 | | 1/2004 |
| WO | WO 2004/010106 A2 | | 1/2004 |
| WO | WO 2004/069849 A2 | | 8/2004 |

(56) References Cited

FOREIGN PATENT DOCUMENTS

| | | |
|---|---|---|
| WO | WO 2004/091763 A2 | 10/2004 |
| WO | WO 2005/040406 A1 | 10/2004 |
| WO | WO 2004/102204 A1 | 11/2004 |
| WO | WO 2004/103565 A2 | 12/2004 |
| WO | WO 2004/105734 A1 | 12/2004 |
| WO | WO-2005002730 A1 | 1/2005 |
| WO | WO 2005/082098 A2 | 2/2005 |
| WO | WO 2005/021151 A1 | 3/2005 |
| WO | WO 2005/049787 A2 | 6/2005 |
| WO | WO 2006/030993 A1 | 3/2006 |
| WO | WO 2006/078841 A1 | 7/2006 |
| WO | WO 2006/096571 A2 | 9/2006 |
| WO | WO 2007/001448 A2 | 1/2007 |
| WO | WO 2007/002490 A2 | 1/2007 |
| WO | WO 2007/024840 A2 | 3/2007 |
| WO | WO 2007/081385 A2 | 7/2007 |
| WO | WO 2007/081387 A1 | 7/2007 |
| WO | WO 2007/089541 A2 | 8/2007 |
| WO | WO 2008/021123 A1 | 8/2007 |
| WO | WO 2007/114794 A1 | 10/2007 |
| WO | WO 2007/121489 A2 | 10/2007 |
| WO | WO 2007/133710 A2 | 11/2007 |
| WO | WO 2007/138178 A2 | 12/2007 |
| WO | WO 2007/139766 A2 | 12/2007 |
| WO | WO 2007/140015 A2 | 12/2007 |
| WO | WO 2007/149432 A2 | 12/2007 |
| WO | WO 2008/091792 A2 | 1/2008 |
| WO | WO 2008/102057 A1 | 8/2008 |
| WO | WO 2008/109176 A2 | 9/2008 |
| WO | WO 2008/121342 A2 | 10/2008 |
| WO | WO 2008/134153 A1 | 11/2008 |
| WO | WO 2009/005680 A1 | 1/2009 |
| WO | WO 2009/011808 A1 | 1/2009 |
| WO | WO-2009048532 A2 | 4/2009 |
| WO | WO 2009/061372 A1 | 5/2009 |
| WO | WO 2009/085215 A1 | 7/2009 |
| WO | WO 2010/004018 A2 | 1/2010 |
| WO | WO-2010014604 A1 | 2/2010 |
| WO | WO 2010/033200 A2 | 3/2010 |
| WO | WO-2010104604 A1 | 9/2010 |
| WO | WO 2010/115154 A1 | 10/2010 |
| WO | WO 2010/148039 A2 | 12/2010 |
| WO | WO 2010/151776 A2 | 12/2010 |
| WO | WO 2011/047870 A1 | 4/2011 |
| WO | WO 2011/056546 A1 | 5/2011 |
| WO | WO 2011/066476 A1 | 6/2011 |
| WO | WO 2011/074960 A1 | 6/2011 |
| WO | WO 2012/012037 A1 | 1/2012 |
| WO | WO-2012019765 A1 | 2/2012 |
| WO | WO 2012/048341 A1 | 4/2012 |
| WO | WO 2012/083225 A2 | 6/2012 |
| WO | WO-2012106546 A2 | 8/2012 |
| WO | WO-2012112970 A2 | 8/2012 |
| WO | WO-2012142611 A2 | 10/2012 |
| WO | WO 2012/149042 A2 | 11/2012 |
| WO | WO 2012/166425 A2 | 12/2012 |
| WO | WO-2013019751 A1 | 2/2013 |
| WO | WO-2013036929 A1 | 3/2013 |
| WO | WO 2013/123125 A1 | 8/2013 |
| WO | WO-2013122996 A1 | 8/2013 |
| WO | WO 2013/177220 A1 | 11/2013 |
| WO | WO 2014/028537 A1 | 2/2014 |
| WO | WO-2014074611 A1 | 5/2014 |
| WO | WO-2014093676 A1 | 6/2014 |
| WO | WO-2014210353 A2 | 12/2014 |
| WO | WO 2005/023331 A2 | 3/2015 |
| WO | WO-2015044428 A1 | 4/2015 |

OTHER PUBLICATIONS

U.S. Appl. No. 14/624,473, filed Feb. 17, 2015, Hindson et al.
U.S. Appl. No. 14/624,484, filed Feb. 17, 2015, Hindson et al.
U.S. Appl. No. 14/680,808, filed Apr. 7, 2015, Hindson et al.
Abate et al., Valve-based flow focusing for drug formation. Appl Phys Lett. 2009;94. 3 pages.
Abate, et al. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.
Advisory Action dated Mar. 21, 2014 for U.S. Appl. No. 13/119,470.
Advisory Action dated May 16, 2014 for U.S. Appl. No. 13/503,588.
Advisory Action mailed Nov. 20, 2013 for U.S. Appl. No. 13/139,326.
Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.
Akselband, "Enrichment of slow-growing marine microorganisms from mixed cultures using gel microdrop (GMD) growth assay and fluorescence-activated cell sorting", J. Exp. Marine Bioi., 329: 196-205 (2006).
Akselband, "Rapid mycobacteria drug susceptibility testing using gel microdrop (GMD) growth assay and flow cytometry", J. Microbiol. Methods, 62:181-197 (2005).
Anna et al., "Formation of dispersions using 'flow focusing' in microchannels", Appln. Phys. Letts. 82:3 364 (2003).
Australian Office Action issued Dec. 17, 2013 for Application No. AU 2010315580.
Boone, et al. Plastic advances microfluidic devices. The devices debuted in silicon and glass, but plastic fabrication may make them hugely successful in biotechnology application. Analytical Chemistry. Feb. 2002; 78A-86A.
Braeckmans et al., Scanning the Code. Modern Drug Discovery. 2003:28-32.
Bransky, et al. A microfluidic droplet generator based on a piezoelectric actuator. Lab Chip. Feb. 21, 2009;9(4):516-20. doi: 10.1039/b814810d. Epub Nov. 20, 2008.
Carroll, "The selection of high-producing cell lines using flow cytometry and cell sorting", Exp. Op. Bioi. Therp., 4:11 1821-1829 (2004).
Chaudhary "A rapid method of cloning functioNal variable-region antibody genese in *Escherichia coli* as single-chain imrnunotoxins" Proc. Nat!. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;18(1):83-101.
Chinese Office Action and search report mailed May 23, 2013 for Application No. CN 200880127116.4.
Chinese office action dated Jun. 18, 2012 for CN Application No. 200880127116.4.
Chou, et al. Disposable Microdevices for DNA Analysis and Cell Sorting. Proc. Solid-State Sensor and Actuator Workshop, Hilton Head, SC. Jun. 8-11, 1998; 11-14.
Clausell-Tormos et al., "Droplet-based microfluidic platforms for the encapsulation and screening of mammalian cells and multicellular organisms", Chem. Biol. 15:427-437 (2008).
De Bruin et al., UBS Investment Research. Q-Series®: DNA Sequencing. UBS Securities LLC. Jul. 12, 2007. 15 pages.
Demirci, et al. Single cell epitaxy by acoustic picolitre droplets. Lab Chip. Sep. 2007;7(9):1139-45. Epub Jul. 10, 2007.
Doerr, "The smallest bioreactor", Nature Methods, 2:5 326 (2005).
Dowding, et al. Oil core/polymer shell microcapsules by interNal phase separation from emulsion droplets. II: controlling the release profile of active molecules. Langmuir. Jun. 7, 2005;21(12):5278-84.
Drmanac et al., Sequencing by hybridization (SBH): advantages, achievements, and opportunities. Adv Biochem Eng Biotechnol. 2002;77 :75-101.
Droplet Based Sequencing (slides) dated (Mar. 12, 2008).
Esser-Kahn, et al. Triggered release from polymer capsules. Macromolecules. 2011; 44:5539-5553.
European office action dated Jan. 23, 2012 for Application No. EP 08865992.5.
European office action dated Apr. 5, 2013 for Application No. EP 08865992.5.

(56) References Cited

OTHER PUBLICATIONS

European office action dated Aug. 29, 2013 for Application No. EP 08865992.5.
European office action dated Dec. 15, 2010 for EP Application No. 08865992.5.
Fisher, et al. A scalable, fully automated process for construction of sequence-ready human exome targeted capture libraries. Genome Biol. 2011;12(1):R1. doi: 10.1186/gb-2011-12-1-r1. Epub Jan. 4, 2011.
Freiberg, et al. Polymer microspheres for controlled drug release. Int J Pharm. Sep. 10, 2004;282(1-2):1-18.
Fu, "A micro fabricated fluorescence-activated cell sorter", Nature Biotech., 17:1109-1111 (1997).
Fulton et al., Advanced multiplexed analysis with the FlowMetrix system. Clin Chem. Sep. 1997;43(9): 1749-56.
Garstecki, et al. Formation of monodisperse bubbles in a microfluidic flow-focusing device. Applied Physics Letters. 2004; 85(13):2649-2651. DOI: 10.1063/1.1796526.
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Ghadessy, et al. Directed evolution of polymerase function by compartmentalized self-replication. Proc Natl Acad Sci U S A. Apr. 10, 2001;98(8):4552-7. Epub Mar. 27, 2001.
Gyarmati, et al. Reversible disulphide formation in polymer networks: a versatile functional group from synthesis to applications. European Polymer Journal. 2013; 49:1268-1286.
Hashimshony, et al. CEL-Seq: Single-Cell RNa-Seq by Multiplexed Linear Amplification. Cell Rep. Sep. 27, 2012;2(3):666-73. doi: 10.1016/j.celrep.2012.08.003. Epub Aug. 30, 2012.
He "Selective Encapsulation of Single Cells and Subcellular Organelles into Picoliter- and Femtoliter-Volume Droplets" ANal. Chem 77: 1539-1544 (2005).
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Huebner, "Quantitative detection of protein expression in single cells using droplet microfluidics", Chem. Commun. 1218-1220 (2007).
Hug, et al. Measurement of the number of molecules of a single mRNA species in a complex mRNA preparation. J Theor Biol. Apr. 21, 2003;221(4):615-24.
International Preliminary Report on Patentability dated Mar. 31, 2011 for PCT/US09/005184.
International Preliminary Report on Patentability dated May 10, 2012 for PCT/US2010/054050.
International Preliminary Report on Patentability dated Jun. 30, 2011 for PCT/US2009/006649.
International Preliminary Report on Patentability dated Jul. 1, 2010 for PCT/US2008/013912.
International Preliminary Report on Patentability dated Sep. 17, 2009 for PCT/US2008/003185 mailed Sep. 17, 2009.
International search report and written opinion dated Jan. 12, 2009 for PCT/US2008/003185.
International search report and written opinion dated Jan. 31, 2011 for PCT/US2010/054050.
International search report and written opinion dated Apr. 3, 2009 for PCT/US2008/013912.
International search report and written opinion dated May 14, 2014 for PCT/US2014/015427.
International search report and written opinion dated May 14, 2015 for PCT/US2014/044398.
International search report and written opinion dated May 16, 2014 for PCT/US2013/074764.
International search report and written opinion dated Aug. 16, 2010 for PCT/US2009/005184.
International search report and written opinion dated Aug. 20, 2014 for PCT/US2014/015424.
International search report and written opinion dated Oct. 2, 2009 for PCT/US2009/004037.
International search report and written opinion dated Oct. 21, 2009 for PCT/US2009/003389.
International search report and written opinion dated Oct. 29, 2008 for PCT/US2008/008563.
International search report and written opinion dated Dec. 16, 2013 for PCT/US2013/054797.
International search report dated Apr. 22, 2009 for PCT/US2009/000664.
Japanese Final Rejection dated Aug. 5, 2014 for Application No. JP 2012-536941.
Japanese Office Action and mailed Jul. 17, 2013 for Application No. JP 2010-539498.
Japanese Office Action mailed Nov. 19, 2013 for Application No. JP 2012-536941.
Khomiakov A et al., [Analysis of perfect and mismatched DNA duplexes by a generic hexanucleotide microchip]. Mol Bioi (Mosk). Jul.-Aug. 2003;37(4):726-41. Russian. Abstract only.
Kim, et al. Albumin loaded microsphere of amphiphilic poly(ethylene glycol)/ poly(alpha-ester) multiblock copolymer. Eur J Pharm Sci. Nov. 2004;23(3):245-51.
Kim, et al. Fabrication of monodisperse gel shells and functioNal microgels in microfluidic devices. Angew Chem Int Ed Engl. 2007;46(11):1819-22.
Koster et al., "Drop-based microfluidic devices for encapsulation of single cells", Lab on a Chip The Royal Soc. of Chem. 8: 1110-1115 (2008).
Kutyavin, et al. Oligonucleotides containing 2-aminoadenine and 2-thiothymine act as selectively binding complementary agents. Biochemistry. Aug. 27, 1996;35(34):11170-6.
Li, Y., et al., "PEGylated PLGA Nanoparticles as protein carriers: synthesis, preparation and biodistribution in rats," JourNal of Controlled Release, vol. 71, pp. 203-211 (2001).
Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Loscertales, I.G., et al., "Micro/Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24:6 703 (Jun. 2006).
Marcus. Gene method offers diagnostic hope. The Wall Street JourNal. Jul. 11, 2012.
Mazutis, et al. Selective droplet coalescence using microfluidic systems. Lab Chip. Apr. 24, 2012;12(10):1800-6. doi: 10.1039/c2lc40121e. Epub Mar. 27, 2012.
Merriman, et al. Progress in ion torrent semiconductor chip based sequencing. Electrophoresis. Dec. 2012;33(23):3397-417. doi: 10.1002/elps.201200424.
Microfluidic ChipShop. Microfluidic product catalogue. Mar. 2005.
Microfluidic ChipShop. Microfluidic product catalogue. Oct. 2009.
Mirzabekov, "DNA Sequencing by Hybridization—a Megasequencing Method and a Diagnostic Tool?" Trends in Biotechnology 12(1): 27-32 (1994).
Mouritzen et al., Single nucleotide polymorphism genotyping using locked nucleic acid (LNa). Expert Rev Mol Diagn. Jan. 2003;3(1):27-38.
Nguyen, et al. In situ hybridization to chromosomes stabilized in gel microdrops. Cytometry. 1995; 21:111-119.
Notice of Allowance dated Jan. 27, 2014 for U.S. Appl. No. 13/139,326.
Oberholzer, et al. Polymerase chain reaction in liposomes. Chem Biol. Oct. 1995;2(10):677-82.
Office action dated Jan. 4, 2010 for U.S. Appl. No. 12/172,186.
Office action dated Jan. 15, 2015 for U.S. Appl. No. 14/250,701.
Office action dated Feb. 10, 2014 for U.S. Appl. No. 13/503,588.
Office action dated Feb. 28, 2013 for U.S. Appl. No. 13/139,326.
Office action dated Apr. 20, 2015 for U.S. Appl. No. 13/966,150.
Office action dated Apr. 24, 2013 for U.S. Appl. No. 13/119,470.

(56) References Cited

OTHER PUBLICATIONS

Office action dated May 20, 2014 for U.S. Appl. No. 14/172,266.
Office action dated May 20, 2014 for U.S. Appl. No. 14/172,326.
Office action dated May 28, 2013 for U.S. Appl. No. 12/529,926.
Office action dated Jul. 30, 2014 for U.S. Appl. No. 12/809,120.
Office action dated Aug. 6, 2013 for U.S. Appl. No. 13/139,326.
Office action dated Aug. 6, 2014 for U.S. Appl. No. 12/529,926.
Office action dated Sep. 10, 2014 for U.S. Appl. No. 14/250,701.
Office action dated Sep. 17, 2013 for U.S. Appl. No. 13/503,588.
Office action dated Oct. 1, 2012 for U.S. Appl. No. 12/529,926.
Office action dated Dec. 5, 2013 for U.S. Appl. No. 13/119,470.
Office Action mailed Apr. 29, 2014 for EP Application No. 08865992.5.
Office Action mailed Dec. 16, 2013 for CN Application No. 201080055990.9.
Office Action mailed May 23, 2013 for CN Application No. 200880127116.4.
Ogawa, et al. Production and characterization of O/W emulsions containing cationic droplets stabilized by lecithin-chitosan membranes. J Agric Food Chem. Apr. 23, 2003;51(9):2806-12.
Okushima, "Controlled production of monodisperse double emulsions by two-step droplet breakup in microfluidic devices", Langmuir, 20:9905-9908 (2004).
Perez, C., et al., "Poly(lactic acid)-poly(ethylene glycol) Nanoparticles as new carriers for the delivery ofplasmid DNa," JourNal of Controlled Release, vol. 75, pp. 211-224 (2001).
Peters, et al. Accurate whole-genome sequencing and haplotyping from 10 to 20 human cells. Nature. Jul. 11, 2012;487(7406):190-5. doi: 10.1038/Nature11236.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Ryan, et al. Rapid assay for mycobacterial growth and antibiotic susceptibility using gel microdrop encapsulation. J Clin Microbiol. Jul. 1995;33(7):1720-6.
Schirinzi et al., Combinatorial sequencing-by-hybridization: aNalysis of the NFI gene. Genet Test. 2006 Spring;10(1):8-17.
Schmitt, "Bead-based multiplex genotyping of human papillomaviruses", J. Clinical Microbial., 44:2 504-512 (2006).
Shah, "Fabrication of mono disperse thermosensitive microgels and gel capsules in micro fluidic devices", Soft Matter, 4:2303-2309 (2008).
Simeonov et al., Single nucleotide polymorphism genotyping using short, fluorescently labeled locked nucleic acid (LNa) probes and fluorescence polarization detection. Nucleic Acids Res. Sep. 1, 2002;30(17):e91.
Sorokin et al., DiscrimiNation between perfect and mismatched duplexes with oligonucleotide gel microchips: role of thermodyNamic and kinetic effects during hybridization. J Biomol Struct Dyn. Jun. 2005;22(6):725-34.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese JourNal Experimental Surgery. May 2005;22(5):639-40.
Tawfik, et al. Man-made cell-like compartments for molecular evolution. Nat Biotechnol. Jul. 1998;16(7):652-6.
Theberge, et al. Microdropelts in microfluidics: an evolving platform for discoveries in chemsitry and biology. Angew Chem Int Ed Engl. Aug. 9, 2010;49(34):5846-68. doi: 10.1002/anie.200906653.
Tubeleviciute, et al. Compartmentalized self-replication (CSR) selection of *Thermococcus litoralis* Sh1B DNa polymerase for diminished uracil binding. Protein Eng Des Sel. Aug. 2010;23(8):589-97. doi: 10.1093/protein/gzq032. Epub May 31, 2010.
Wang et al., Single nucleotide polymorphism discrimiNation assisted by improved base stacking hybridization using oligonucleotide microarrays. Biotechniques. 2003;35:300-08.
Wang, et al. A novel thermo-induced self-bursting microcapsule with magnetic-targeting property. Chemphyschem. Oct. 5, 2009;10(14):2405-9.
Weaver, "Rapid clonal growth measurements at the single-cell level: gel microdroplets and flow cytometry", Biotechnology, 9:873-877 (1991).
Whitesides, "Soft lithography in biology and biochemistry", Annual Review of Biomedical Engineering, 3:335-373 (2001).
Williams, et al. Amplification of complex gene libraries by emulsion PCR. Nat Methods. Jul. 2006;3(7):545-50.
Woo, et al. G/C-modified oligodeoxynucleotides with selective complementarity: synthesis and hybridization properties. Nucleic Acids Res. Jul. 1, 1996;24(13):2470-5.
Xia, "Soft lithography", Annual Review of Material Science, 28: 153-184 (1998).
Yamamoto, et al. Chemical modification of Ce(IV)/EDTA-base artificial restriction DNa cutter for versatile manipulation of doulbestranded DNa. Nucleic Acids Research. 2007; 35(7):e53.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functioNalized nucleosides via the RAFT process. Biomacromolecules. Nov. 2008;9(11):3321-31. doi: 10.1021/bm800867n. Epub Oct. 9, 2008.
Zhao, J., et al., "Preparation of hemoglobin-loaded Nano-sized particles with porous structure as oxygen carriers," Biomaterials, vol. 28, pp. 1414-1422 (2007).
Zimmermann et at., Microscale production of hybridomas by hypoosmolar electrofusion. Hum• Antibodies Hybridomas. Jan. 1992;3(1 ): 14-8.
Zong, et al. Genome-wide detection of single-nucleotide and copynumber variations of a single human cell. Science. Dec. 21, 2012;338(6114):1622-6. doi: 10.1126/science.1229164.
International search report and written opinion dated Aug. 19, 2015 for PCT/US2015/025197.
Office action dated Sep. 16, 2015 for U.S. Appl. No. 14/175,973.
Office action dated Sep. 25, 2015 for U.S. Appl. No. 14/250,701.
Office action dated Oct. 9, 2015 for U.S. Appl. No. 14/680,808.
Office action dated Nov. 6, 2015 for U.S. Appl. No. 13/966,150.
European search report and opinion dated Feb. 2, 2016 for EP Application No. 13829413.
Office action dated Jan. 29, 2016 for U.S. Appl. No. 14/175,935.
Office action dated Feb. 23, 2016 for U.S. Appl. No. 14/104,650.
Office action dated Mar. 1, 2016 for U.S. Appl. No. 14/250,701.
Office action dated Mar. 4, 2016 for U.S. Appl. No. 14/175,973.
Office action dated Mar. 14, 2016 for U.S. Appl. No. 14/680,808.
Shimkus, et al. A chemically cleavable biotinylated nucleotide: usefulness in the recovery of protein-DNA complexes from avidin affinity columns. Proc Natl Acad Sci U S A. May 1985;82(9):2593-7.
Office action dated Jun. 23, 2016 for U.S. Appl. No. 14/624,473.
Office action dated Jun. 24, 2016 for U.S. Appl. No. 14/624,468.
U.S. Appl. No. 15/200,928, filed Jul. 1, 2016, Hindson et al.
Baret, et al. Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
European search report and opinion dated Jul. 25, 2016 for EP Application No. 13862194.1.
European search report and opinion dated Jul. 25, 2016 for EP Application No. 14748569.2.
European search report and opinion dated Jul. 25, 2016 for EP Application No. 14817610.
European search report and opinion dated Jul. 26, 2016 for EP Application No. 14749595.6.
Grasland-Mongrain, et al. Droplet coalescence in microfluidic devices. Jan.-Jul. 2003. 31 pages. http://www.eleves.ens.fr/home/grasland/rapports/stage4.pdf.
Makino, et al. Preparation of hydrogel microcapsules: Effects of preparation conditions upon membrane properties. Colloids and Surfaces B: Biointerfaces. Nov. 1998; 12(2), 97-104.

(56) References Cited

OTHER PUBLICATIONS

Nagashima, et al. Preparation of monodisperse poly (acrylamide-co-acrylic acid) hydrogel microspheres by a membrane emulsification technique and their size-dependent surface properties. Colloids and Surfaces B: Biointerfaces. Jun. 15, 1998; 11(1-2), 47-56.
Office action dated Aug. 5, 2016 for U.S. Appl. No. 14/175,935.
Office action dated Aug. 11, 2016 for U.S. Appl. No. 14/250,701.
Office action dated Sep. 15, 2016 for U.S. Appl. No. 15/200,928.
Turner, et al. Methods for genomic partitioning. Annu Rev Genomics Hum Genet. 2009;10:263-84. doi: 10.1146/annurev-genom-082908-150112. Review.
Abate, et al. Beating Poisson encapsulation statistics using close-packed ordering. Lab Chip. Sep. 21, 2009;9(18):2628-31. doi: 10.1039/b909386a. Epub Jul. 28, 2009.
Attia, et al. Micro-injection moulding of polymer microfluidic devices. Microfluidics and Nanofluidics. 2009; 7(1):1-28.
Brouzes, et al. Droplet microfluidic technology for single-cell high-throughput screening. Proc. Natl. Acad. Sci. USA. Aug. 25, 2009;106(34):14195-200. doi: 10.1073/pnas.0903542106. Epub Jul. 15, 2009.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Chokkalingam, et al. Probing cellular heterogeneity in cytokine-secreting immune cells using droplet-based microfluidics. Lab Chip. Dec. 21, 2013;13(24):4740-4. doi: 10.1039/c3lc50945a.
Chu, et al. Controllable monodisperse multiple emulsions. Angew Chem Int Ed Engl. 2007;46(47):8970-4.
Draper, et al. Compartmentalization of electrophoretically separated analytes in a multiphase microfluidic platform. Anal Chem. Jul. 3, 2012;84(13):5801-8. doi: 10.1021/ac301141x. Epub Jun. 13, 2012.
Dressler, et al. Droplet-based microfluidics enabling impact on drug discovery. J Biomol Screen. Apr. 2014;19(4):483-96. doi: 10.1177/1087057113510401. Epub Nov. 15, 2013.
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Fredrickson, et al. Macro-to-micro interfaces for microfluidic devices. Lab Chip. Dec. 2004;4(6):526-33. Epub Nov. 10, 2004.
Granieri, Lucia. Droplet-based microfluidics and engineering of tissue plasminogen activator for biomedical applications. Ph.D. Thesis, Nov. 13, 2009 (131 pages).
Guo, et al. Droplet microfluidics for high-throughput biological assays. Lab Chip. Jun. 21, 2012;12(12):2146-55. doi: 10.1039/c2lc21147e. Epub Feb. 9, 2012.
Jena, et al. Cyclic olefin copolymer based microfluidic devices for biochip applications: Ultraviolet surface grafting using 2-methacryloyloxyethyl phosphorylcholine. Biomicrofluidics. Mar. 2012;6(1):12822-1282212. doi: 10.1063/1.3682098. Epub Mar. 15, 2012.
Jung, et al. Micro machining of injection mold inserts for fluidic channel of polymeric biochips. Sensors. 2007; 7(8):1643-1654.
Kim, et al. Rapid prototyping of microfluidic systems using a PDMS/polymer tape composite. Lab Chip. May 7, 2009;9(9):1290-3. doi: 10.1039/b818389a. Epub Feb. 10, 2009.
Klein, et al. Droplet barcoding for single-cell transcriptomics applied to embryonic stem cells. Cell. May 21, 2015;161(5):1187-201. doi: 10.1016/j.cell.2015.04.044.
Lagus, et al. A review of the theory, methods and recent applications of high-throughput single-cell droplet microfluidics. J. Phys. D: Appl. Phys. (2013) 46:114005. (21 pages).
Lowe, Adam J. Norbornenes and [n]polynorbornanes as molecular scaffolds for anion recognition. Ph.D. Thesis (May 2010). (361 pages).
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Mair, et al. Injection molded microfluidic chips featuring integrated interconnects. Lab Chip. Oct. 2006;6(10):1346-54. Epub Jul. 31, 2006.
Matochko, et al. Uniform amplification of phage display libraries in monodisperse emulsions. Methods. Sep. 2012;58(1):18-27. doi: 10.1016/j.ymeth.2012.07.012. Epub Jul. 20, 2012.
Moore, et al. Behavior of capillary valves in centrifugal microfluidic devices prepared by three-dimensional printing. Microfluidics and Nanofluidics. 2011; 10(4):877-888.
Navin. The first five years of single-cell cancer genomics and beyond. Genome Res. Oct. 2015;25(10):1499-507. doi: 10.1101/gr.191098.115.
Novak, et al. Single cell multiplex gene detection and sequencing using microfluidically generated agarose emulsions. Angew Chem Int Ed Engl. Jan. 10, 2011;50(2):390-5. doi: 10.1002/anie.201006089.
Office action dated Oct. 12, 2016 for U.S. Appl. No. 14/316,447.
Rotem, et al. High-Throughput Single-Cell Labeling (Hi-SCL) for RNA-Seq Using Drop-Based Microfluidics. PLoS One. May 22, 2015;10(5):e0116328. doi: 10.1371/journal.pone.0116328. eCollection 2015.
Rotem, et al. Single Cell Chip-Seq Using Drop-Based Microfluidics. Abstract #50. Frontiers of Single Cell Analysis, Stanford University Sep. 5-7, 2013.
Seiffert, et al. Smart microgel capsules from macromolecular precursors. J Am Chem Soc. May 12, 2010;132(18):6606-9. doi: 10.1021/ja102156h.
Tewhey, et al. Microdroplet-based PCR enrichment for large-scale targeted sequencing. Nat Biotechnol. Nov. 2009;27(11):1025-31. doi: 10.1038/nbt.1583. Epub Nov. 1, 2009.
Tonelli, et al. Perfluoropolyether functional oligomers: unusual reactivity in organic chemistry. Journal of Fluorine Chemistry. 2002; 118(1)"107-121.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Zhu, et al. Synthesis and self-assembly of highly incompatible polybutadienepoly(hexafluoropropoylene oxide) diblock copolymers. Journal of Polymer Science Part B: Polymer Physics. 2005; 43(24):3685-3694.
Altemos et al., "Genomic Characterization of Large Heterochromatic Gaps in the Human Genome Assembly," PLOS Computational Biology, May 15, 2014, vol. 10, Issue 5, 14 pages.
Amini, S. et al. "Haplotype-resolved whole-genome sequencing by contiguity-preserving transposition and combinatorial indexing" Nature Genetics (2014) 46:1343-1349 doi:10.1038/ng.3119.
Anonymous, "Oligo(dT)25 cellulose beads" NEB (2012) Retrieved from the Internet:http://www.neb.com/~/media/Catalog/All-Products/286CA51268E24DE1B06F1CB288698B54/Datacards%20or%Manuals/S1408Datasheet-Lot0011205.pdf.
Anonymous, "Oligotex Handbook" Qiagen (2012) XP055314680, Retrieved from the Internet: URL:http://www.qiagen.com/de/resources/download.apsx?id=f9fald98-d54d-47e7-a20b-8b0cb8975009&lang=en.
Anonymous: "Viscosity-Basic concepts" (2004) XP055314117, Retrieved from the Internet: URL:http://lhtc.epfl.ch/webdav/site/lhtc/shared/import/migration/2 VISCOSITY.pdf.
Bodi, K. et al. "Comparison of Commercially Available Target Enrichment Methods for Next-Generation Sequencing" J Biomolecular Techniques (2013) 24:73-86.
Christiansen et al. "The Covalent Eukaryotic Topoisomerase I-DNA Intermediate Catalyzes pH-dependent Hydrolysis and Alcoholysis" J Biol Chem (Apr. 14, 1994) 269(15):11367-11373.
Coufal, et al. L1 retrotransposition in human neural progenitor cells. Nature. Aug. 27, 2009;460(7259):1127-31. doi: 10.1038/nature08248. Epub Aug. 5, 2009.
Doshi, et al. Red blood cell-mimicking synthetic biomaterial particles. Proceedings of the National Academy of Sciences 106.51 (2009): 21495-21499.

(56) References Cited

OTHER PUBLICATIONS

Fan, et al. Noninvasive diagnosis of fetal aneuploidy by shotgun sequencing DNA from maternal blood. Proc Natl Acad Sci U S A. Oct. 21, 2008;105(42):16266-71. doi: 10.1073/pnas.0808319105. Epub Oct. 6, 2008.

Fang, et al. Flouride-cleavable biotinylation phosphoramidite for 5'-end-labeling and affinity purification of synthetic oligonucleotides. Nucleic Acids Res. Jan. 15, 2003;31(2):708-15.

Frampton, G.M. et al. "Development and validation of a clinical cancer genomic profiling test based on massively parallel DNA sequencing" Nature Biotechnology (2013) 31(11):1023-1031. doi:10.1038/nbr.2696.

Gericke, et al. Functional cellulose beads: preparation, characterization, and applications. Chemical reviews 113.7 (2013): 4812-4836.

He, J. et al. "Genotyping-by-sequencing (GBS), an ultimate marker-assisted selections (MAS) tool to accelerate plant breeding" Frontiers in Plant Sci (Sep. 30, 2014) 5:1-8.

Hjerten, et al. General methods to render macroporous stationary phases nonporous and deformable, exemplified with agarose and silica beads and their use in high-performance ion-exchange and hydrophobic-interaction chromatography of proteins. Chromatographia 31.1-2 (1991): 85-94.

Ioannidis, N. Manufacturing of Agarose-Based Chromatographic Adsorbents With Controlled Pore and Particle Sizes. A thesis submitted to The University of Birmingham for the degree of Doctor of Philosophy. 2009.

Lee, J-H. et al. "Fluorescent in situ sequencing (FISSEQ) of RNA for gene expression profiling in intact cells and tissues" Nature Protocols (Feb. 12, 2015) 10(3):442-458.

Morgan, et al. Chapter 12: Human microbiome analysis. PLoS Comput Biol. 2012;8(12):e1002808. doi: 10.1371/journal.pcbi.1002808. Epub Dec. 27, 2012.

Mozhanova, A.A. et al. "Local elastic properties of biological materials studied by SFM" (2003) XP055314108, Retrieved from the Internet: URL:http://www.ntmdt.com/data/media/files/publications/2003/08.08_a.a.mozhanova_n.i.n_english.pdf.

Muotri, et al. L1 retrotransposition in neurons is modulated by MeCP2. Nature. Nov. 18, 2010;468(7322):443-6. doi: 10.1038/nature09544.

Oligotex Handbook. For purification of poly A+ RNA from total RNA and directly from cultured cells or tissues as well as purification of polyadenylated in vitro transcripts. Jun. 2012.

Pantel, et al. Detection methods of circulating tumor cell. J Thorac Dis. Oct. 2012;4(5):446-7. doi: 10.3978/j.issn.2072-1439.2012.08.15.

Patel, et al. Single-cell RNA-seq highlights intratumoral heterogeneity in primary glioblastoma. Science. Jun. 20, 2014;344(6190):1396-401. doi: 10.1126/science.1254257. Epub Jun. 12, 2014.

Picot, J. et al. "A biomimetic microfluidic chip to study the circulation and mechanical retention of red blood cells in the spleen" Am J Hematology (Jan. 12, 2015) 90(4):339-345.

Ram, et al. Strategy for microbiome analysis using 16S rRNA gene sequence analysis on the illumina sequencing platform. Syst Biol Reprod Med. Jun. 2011;57(3):162-70. doi: 10.3109/19396368.2011.555598. Epub Mar. 1, 2011.

Richardson, et al. Novel inhibition of archaeal family-D DNA polymerase by uracil. Nucleic acids research 41.7 (2013): 4207-4218.

Rogozin, et al. A highly conserved family of inactivated archaeal B family DNA polymerases. Biol Direct. Aug. 6, 2008;3:32. doi: 10.1186/1745-6150-3-32.

Schmeider, et al. Fast identification and removal of sequence contamination from genomic and metagenomic datasets. PLoS One. Mar. 9, 2011;6(3):e17288. doi: 10.1371/journal.pone.0017288.

Shuttleworth, et al. Recognition of the pro-mutagenic base uracil by family B DNA polymerases from archaea. J Mol Biol. Mar. 26, 2004;337(3):621-34.

Tayyab, S. et al. "Size exclusion chromatography and size exclusion HPLC of proteins" Biochem Ed, Pergamon, (1991) 19(3):149-152.

Zheng, X.Y. et al. "Haplotyping germline and cancer genomes with high-throughput linked-read sequencing" Nature Biotech (Feb. 1, 2016) 34(3):303-311.

Fu, A.Y., et al., "A microfabricated fluorescence-activated cell sorter," Nature Biotechnology, vol. 17, pp. 1109-1111 (1999).

\* cited by examiner

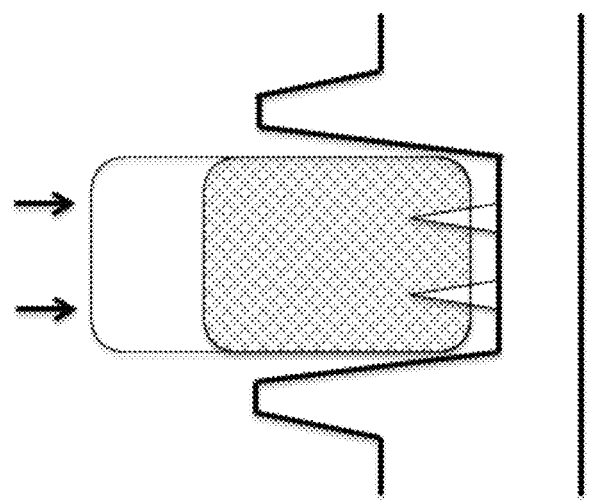
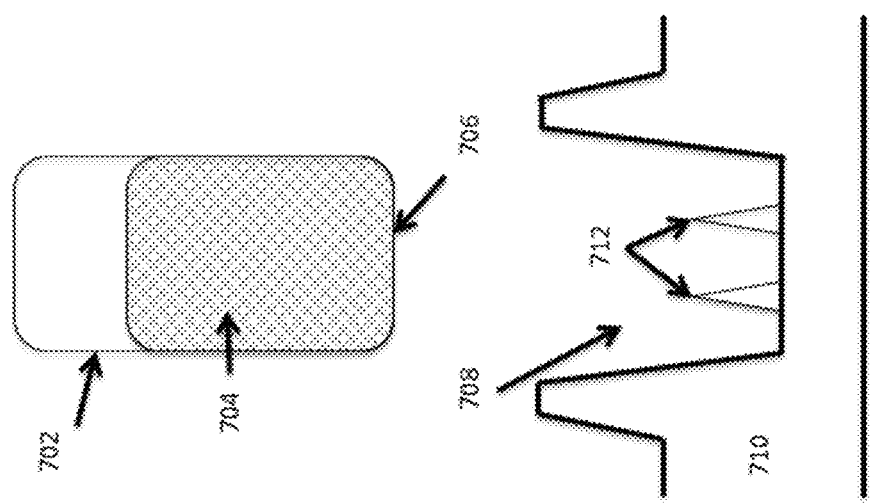
Figure 7A
Figure 7B

FLUIDIC DEVICES, SYSTEMS, AND METHODS FOR ENCAPSULATING AND PARTITIONING REAGENTS, AND APPLICATIONS OF SAME

CROSS-REFERENCE

This application claims priority to U.S. Provisional Patent Application No. 61/977,804, filed Apr. 10, 2014, the full disclosure of which is incorporated herein by reference in its entirety for all purposes.

BACKGROUND

The field of life sciences has experienced dramatic advancement over the last two decades. From the broad commercialization of products that derive from recombinant deoxyribonucleic acid (DNA) technology, to the simplification of research, development and diagnostics, enabled by critical research tools, such as the polymerase chain reaction, nucleic acid array technologies, robust nucleic acid sequencing technologies, and more recently, the development and commercialization of high throughput next generation sequencing technologies. All of these improvements have combined to advance the fields of biological research, medicine, diagnostics, agricultural biotechnology, and myriad other related fields by leaps and bounds.

None of these technologies generally exist in a vacuum, but instead are integrated into a broader workflow that includes upstream components of sample gathering and preparation, to the downstream components of data gathering, deconvolution, interpretation and ultimately exploitation. Further, each of these advancements, while marking a big step forward for their fields, has tended to expose critical bottlenecks in the workflows that must, themselves, evolve to fit the demands of the field. For example, genome sequencing is bounded on both ends by critical workflow issues, including, in many cases, complex and labor intensive sample preparation processes, just to be able to begin sequencing nucleic acids from sample materials. Likewise, once sequence data is obtained, there is a complex back-end informatics requirement in order to deconvolve the sequence data into base calls, and then assemble the determined base sequences into contiguous sequence data, and ultimately align that sequence data to whole genomes for a given organism.

One critical bottleneck for many of these technologies lies not in their ability to generate massive amounts of data, but in the ability to more specifically attribute that data to a portion of a complex sample, or to a given sample among many multiplexed samples.

SUMMARY

Devices, methods and systems of the present disclosure provide solutions to challenges in various fields, including the challenges described above. The present disclosure provides devices, systems and methods for the generation of encapsulated reagents as well as multiplexed partitions that include these encapsulated reagents for use in a variety of applications.

The devices, systems and methods of the present disclosure employ microfluidic systems in the generation of monodisperse populations of microcapsules or beads that may have reagents such as biological reagents associated therewith. Also provided are devices, systems and methods for selectively and controllably partitioning these microcapsules or beads into droplets in emulsions for use in performing further reactions and/or analyses. Also provided are the various component parts of the devices and systems as well as interface components for facilitating interaction between such components.

An aspect of the disclosure provides a method for partitioning microcapsules. The method can include providing an aqueous fluid comprising a suspension of microcapsules and flowing the aqueous fluid into a droplet generation junction comprising a partitioning fluid to form a population of droplets of the aqueous fluid in the partitioning fluid. The flow rate of the aqueous fluid can be such that no more than 50% of droplets of the population of droplets are unoccupied by a microcapsule from the suspension of microcapsules.

In some embodiments, the flow rate is such that no more than 25% of the droplets of the population of droplets are unoccupied by a microcapsule. In some embodiments, the flow rate is such that no more than 10% of the droplets of the population of droplets are unoccupied by a microcapsule. In some embodiments, the flow rate is such that no more than 50%, 45%, 40%, 35%, 30%, 25%, 20%, 15%, 10%, 5%, 2% or 1% of the population of droplets are unoccupied by a microcapsule.

In some embodiments, fewer than 25% of droplets of the population of droplets comprise more than one microcapsule. In some embodiments, fewer than 20% of droplets of the population of droplets comprise more than one microcapsule. In some embodiments, fewer than 15% of droplets of the population of droplets comprise more than one microcapsule. In some embodiments, fewer than 10% of droplets of the population of droplets comprise more than one microcapsule. In some embodiments, fewer than 5% of droplets of the population of droplets comprise more than one microcapsule.

In some embodiments, at least 80% of droplets of the population of droplets comprise a single microcapsule. In some embodiments, at least 90% of droplets of the population of droplets comprise a single microcapsule. In some embodiments, at least 95% of droplets of the population of droplets comprise a single microcapsule. In some embodiments, at least 70%, 75%, 80%, 85%, 90%, 95%, 98% or 99% of droplets of the population of droplets comprise a single microcapsule.

In some embodiments, the droplet generation junction can be in a microfluidic channel network of a microfluidic device. In some embodiments, the microfluidic channel network can comprise a first channel segment fluidly connecting a source of microcapsules to the droplet generation junction. The microfluidic channel network can also comprise a second channel segment connecting a source of partitioning fluid to the droplet generation junction, and a third channel segment fluidly connected to the droplet generation junction providing an outlet to the droplet generation junction.

In some embodiments, the flow rate can be provided by providing one or more pressure differentials across the first and second channel segments. In some embodiments, the first and/or second channel segments can have cross-sectional dimensions that provide the flow rate such that no more than 50% of droplets of the population of droplets are unoccupied by a microcapsule from the suspension of microcapsules. In some embodiments, the microfluidic channel network can further comprise one or more flow controlling structures within the first channel segment that provide the flow rate.

In some embodiments, the microcapsules of the suspension of microcapsules have a mean cross-sectional dimension and a coefficient of variation in cross-sectional dimension of no greater than 10%. In some embodiments, the microcapsules of the suspension of microcapsules have a mean cross-sectional dimension and a coefficient of variation in cross-sectional dimension of no greater than 10%, 8%, 6%, 4%, 2% or 1%.

An additional aspect of the disclosure provides a method for partitioning microcapsules. The method can include flowing an aqueous fluid comprising a suspension of microcapsules into a droplet generation junction comprising a partitioning fluid. During a window of droplet generation, the microcapsules can be flowing into the droplet generation junction at a frequency that varies less than 30%. The method can also include partitioning the microcapsules in the partitioning fluid during the window of droplet generation. In some embodiments, the frequency is greater than 50 Hz. In some embodiments, the frequency is greater than 500 Hz. In some embodiments, the frequency is greater than 1000 Hz. In some embodiments, the frequency is greater than 50 Hz, 100 Hz, 250 Hz, 500 Hz, 750 Hz, 1000 Hz, 1250 Hz, 1500 Hz, 1750 Hz or 2000 Hz.

In some embodiments, during the window of droplet generation, the microcapsules flow into the droplet generation junction at a frequency that varies less than 20%. In some embodiments, during the window of droplet generation, the microcapsules flow into the droplet generation junction at a frequency that varies less than 10%. In some embodiments, during the window of droplet generation, the microcapsules flow into the droplet generation junction at a frequency that varies less than 5%. In some embodiments, during the window of droplet generation, the microcapsules flow in the droplet generation junction at a frequency that varies less than 30%, 25%, 20%, 15%, 10%, 5%, 2% or 1%.

In some embodiments, flowing the aqueous fluid comprising the suspension of microcapsules in the droplet generation junction comprising a partitioning fluid can comprise flowing the aqueous fluid through a microfluidic channel fluidly connected to the droplet generation junction. The microfluidic channel can include a region that regulates the flow (e.g., flow rate) of the microcapsules.

An additional aspect of the disclosure provides a method for producing microcapsules. The method can include providing a gel precursor in an aqueous fluid and flowing the aqueous fluid having the gel precursor through a fluid conduit that is fluidly connected to a droplet generation junction comprising a partitioning fluid. The partitioning fluid can comprise a gel activation agent. The method can also include forming droplets of the aqueous fluid in the partitioning fluid, where, within the droplets, the gel activation agent contacts the gel precursor to form gel microcapsules. In some embodiments, the aqueous fluid can also comprise a biological molecule, where, for example, the biological molecule can become entrained in the gel microcapsules.

An additional aspect of the disclosure provides a method for partitioning microcapsules. The method can include flowing an aqueous fluid comprising a suspension of a monodisperse population of microcapsules into a droplet generation junction. The monodisperse population can have a mean cross-sectional dimension and a coefficient of variation in cross-sectional dimension of no greater than 10%. The method can also include introducing a partitioning fluid into the droplet generation junction and separating the aqueous fluid into droplets within the partitioning fluid, where the droplets contain one or more microcapsules.

An additional aspect of the disclosure provides a microfluidic system. The microfluidic system can include a microfluidic channel network comprising at least first, second and third channel segments in fluid communication with a droplet generation junction. The first channel segment can be fluidly connected to a first fluid source that comprises a first fluid that comprises an aqueous fluid. The aqueous fluid can comprise a plurality of microcapsules disposed therein. Moreover, the second channel segment can be fluidly connected to a second fluid source that comprises a second fluid that is immiscible with the aqueous fluid. The microfluidic system can also include a flow control system connected to the microfluidic channel network. The flow control system can subject the first fluid and second fluid to flow into the droplet generation junction to generate droplets that comprise microcapsules; and can subject the droplets to flow into the third channel segment such that at least 75% of the droplets comprise at least one microcapsule and fewer than 25% of the droplets comprise more than one microcapsule.

An additional aspect of the disclosure provides a microfluidic system. The microfluidic system can include a microfluidic channel network. The microfluidic channel network can comprise a first channel segment coupled to a source of a first aqueous fluid that comprises a suspension of microcapsules; at least one second channel segment coupled to a source of a second aqueous fluid, the first and second channel segments in fluid communication at a first junction that brings the first aqueous fluid in contact with the second aqueous fluid; and a third channel segment coupled to the first junction and intersecting at least one fourth channel segment at a second junction. The at least one fourth channel segment can be coupled to a source of a fluid that is immiscible with the first and second aqueous fluids. Moreover, the second junction can partition the first and second aqueous fluids into droplets within the fluid. The microfluidic system can also include a flow control system operably coupled to the microfluidic channel network. The flow control system can subject the first, second and third fluids to flow through the microfluidic channel network to form droplets comprising the first and second aqueous fluids in the fluid, at a frequency of at least 50 Hz and that varies less than 20%.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

FIGS. 7A and 7B schematically illustrates an example of interfacing fluid containing vessels with a fluid reservoir on a device.

DETAILED DESCRIPTION

I. General

Figure 1A:
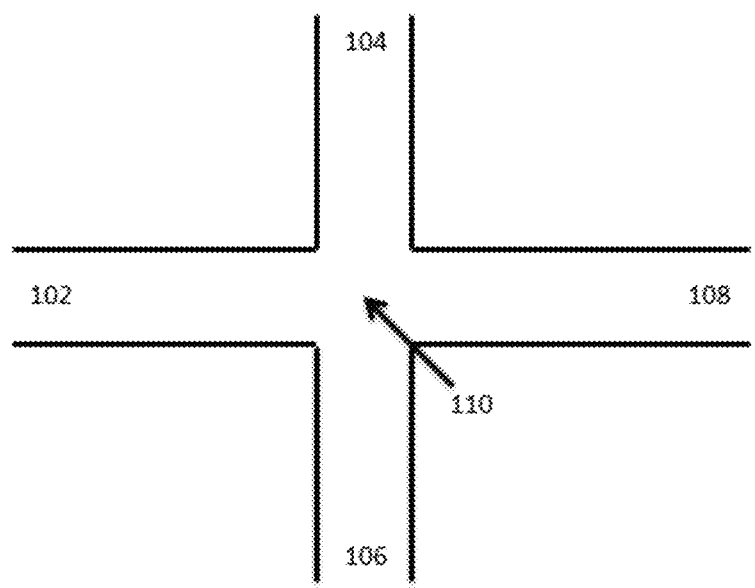
FIGS. 1A, 1B and 1C provide schematic illustrations of example partition or droplet generating fluidic channel junctions.

The present disclosure provides devices, systems and methods that are particularly useful in managing complex samples for analysis using high throughput analytical systems, including, for example, high throughput nucleic acid analysis systems, such as nucleic acid arrays, nucleic acid sequencing systems, nucleic acid amplification and quantitation systems, or the like. In particular, the devices, systems and methods described herein are particularly useful in providing encapsulated reagents or reagent systems, and co-partitioning these reagents with sample components for further reaction and/or analysis. This co-partitioning of reagents and sample components can be used, for example, in reducing the complexity of the sample material by segregating portions of the sample to different partitions. Further, by also segregating reagents, one can subject each sample portion to a different reaction, including for example, the application of unique identifiers to different sample components, e.g., attachment of a discrete barcode or tagging reagents to the discrete sample components.

Particularly elegant examples of these co-partitioning approaches are described in Published International Patent Application No. WO2014/028537, and U.S. patent application Ser. Nos. 14/104,650 (filed Dec. 12, 2013), 14/175,935 (filed Feb. 7, 2014), 14/175,973 (filed Feb. 7, 2014), and 61/937,344 (filed Feb. 7, 2014), the full disclosures of each of which are incorporated herein by reference in their entirety for all purposes.

By way of example, one particularly elegant approach provides a polymer microcapsule composition that includes nucleic acid barcode sequences bound to the microcapsule, where the barcodes associated with a given microcapsule have substantially the same sequence of nucleotides, but where different discrete microcapsules will have different barcode sequences associated with such microcapsules. Each of these microcapsules is then contacted with a portion of a sample fluid, such as a sample fluid that includes a template nucleic acid from a sample material. The mixture of sample material including the template nucleic acid and the microcapsule is then partitioned into a small volume, such as a droplet in a water in oil emulsion, such that the microcapsule and a portion of the sample material are contained within the same droplet. In addition to controlling the droplet generation process to provide a desired number of microcapsules in a given partition, the sample material and emulsion process also may be controlled to provide for a desired amount of sample material, e.g., sample nucleic acid material, within each partition, e.g., to provide a single template molecule or a desired level of genome coverage within a given partition, or other desired level of sample materials.

Within the partition, the barcode sequence is reacted with the sample material, e.g., the template nucleic acid to effectively tag the sample material or a portion thereof. For example, by reacting the barcode sequence with the template, e.g., through amplification of the template sequence using the barcode sequence as an extension primer, one can effectively "attach" the barcode sequence to the replicated or amplified template. Similarly, replication of the extended primer produces a complement of the template along with a complement to the barcode, again, effectively attaching the barcode to the template. The presence or attachment of the barcode sequence, or its complement, on or to the amplified template molecule, or its complement, then allows some level of attribution of sequence reads that include that barcode to the same portion of sample material, e.g., the same template molecule or the same sample components, that was originally allocated to that partition.

In many cases, the molecule that includes the barcode sequence or sequences may also include functional elements that are used in subsequent processing of the amplified template sequences. These functional sequences include, for example, primer sequences (e.g., targeted or universal), primer recognition sequences, sequences that can form secondary structures, either within the sequence, or upon replication of the sequence, enrichment sequences, e.g., that are used as affinity purification sequences, immobilization sequences, probe sequences, reverse complement or hairpin sequences, or any of a variety of other functional sequences.

There are a wide variety of other high-value applications for such partitioning and barcoding or tagging processes. The present disclosure advantageously provides devices, systems and methods that can greatly facilitate the generation of such partitioned compositions or components thereof.

II. Fluidic Systems for Producing Encapsulated Reagents and Partitioned Reactions The present disclosure provides improved fluidic systems, and particularly improved microfluidic systems, that are useful for both the generation of encapsulated reagents, as well as in the partitioning of those encapsulated reagents for use in subsequent reactions and/or analyses. As used herein, microfluidic systems typically denote fluidic systems that employ one or more fluid conduits, channels, chambers, or the like that include one or more interior cross-sectional dimensions, e.g., depth, length or width, that are less than 1000 microns, less than 200 microns, less than 100 microns, and in some cases, less than about 50 microns, or even less than about 20 microns. In some cases, one or more cross-sectional dimensions may be about 20 microns or less or 10 microns or less. Typically, these microfluidic channels or chambers will have at least one cross-sectional dimension of between about 1 and about 100 microns.

As will be appreciated, reference to encapsulated reagents is not intended to limit the scope of such reagents to completely enclosed capsules, but is intended to reflect any of a variety of methods of associating reagents with a given particle, bead, or other solid or semi-solid particle phase. In particular, encapsulation generally refers to the entrainment or other attachment, coupling, or association of a particular species with a solid or semi-solid particle, bead, enclosure, partition or droplet, and is not limited to compositions in which the species is entirely or partially enclosed within a larger structure.

In some aspects, encapsulated reagents are associated with microcapsules that are generally spherical in shape, although they may be elongated, plug shaped, or otherwise vary in their specific shape. In some cases, microcapsules will have one or more cross-sectional dimensions that are less than 200 microns, less than 150 microns, or less than about 100 microns. In some cases, microcapsules of the present disclosure have one or more cross-sectional dimensions that are between about 10 and about 200 microns, between about 20 and 150 microns, between about 30 and 125 microns, in many cases between about 40 and about 100 microns, and still other cases, between about 50 and about 75 microns.

While the dimensions of the microcapsules can be an important consideration, in many applications the variability in those dimensions is also an important consideration. In particular, for example, the transport of a microcapsule through a microfluidic system can be significantly impacted by the size of that microcapsule. For example simple flow resistance may be greater for much larger microcapsules than for smaller microcapsules. Similarly, propensity for clogging may be greater for larger microcapsules than for smaller microcapsules. In either event, flow rates of microcapsules through a microfluidic system may be greatly impacted by the size of the microcapsule. Accordingly, in certain aspects, the microcapsules of described herein, will be provided as a population of microcapsules having substantially monodisperse cross-sectional dimensions. In terms of cross-sectional dimensions, the phrase substantially monodisperse refers to a population that deviates (e.g., expressed as a coefficient of variation and stated as a percentage) from the mean cross-sectional dimension by no more than 50%, no more than 40%, no more than 30%, no more than 20%, or in some cases, no more than 10%.

Whether in the context of generating microcapsules for use in entrainment or encapsulation of reagents, or in the partitioning of aqueous fluids within non-aqueous droplets, the devices and systems of the present disclosure can employ a similar architecture. In a simplified example, this architecture may include a first channel segment that is fluidly connected to a first junction that fluidly connects the first channel segment with a second channel segment and a third channel segment. The second channel segment delivers to the junction a second fluid that is immiscible with the first aqueous fluid, such as an oil, that allows for the formation of aqueous droplets within the stream of immiscible fluid. This second fluid may be referred to herein as the dispersion fluid, partitioning fluid or the like. The flow of the first and second fluids through the junction and into the third channel segment is controlled such that droplets of the first fluid are dispensed into a flowing stream of the second fluid within the third channel segment. A variety of modifications to this basic structure are available to better control droplet formation and to bring in additional fluid streams. As used herein, the control of fluid flows encompasses both active control of fluid flows through the application of greater or lesser driving forces to cause that fluid flow. Additionally, flows may be controlled in whole or in part, by controlling the flow characteristics of one or more of the fluids and/or the conduits through which they are flowing. For example, fluid flow may be controlled by providing higher flow resistance within a conduit, e.g., through providing a higher viscosity, narrower conduit dimension, or providing larger or smaller microcapsules within a fluid stream, or any combination of the foregoing. In some cases, control is imparted through several of controlled driving force, controlled conduit dimensions, and controlled fluid properties, e.g., viscosity or particle composition.

Figure 1B:
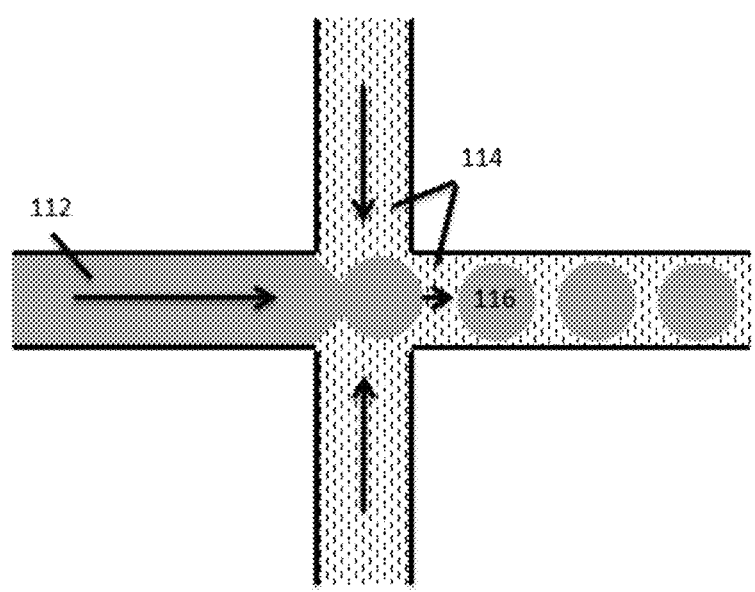

FIG. 1A provides a schematic illustration of an exemplary basic channel architecture for generating droplets in a channel. As shown, first channel segment 102, second channel segment 104, third channel segment 106 and fourth channel segment 108 are all provided in fluid communication at first junction 110. FIG. 1B schematically illustrates droplet formation within the channel architecture of FIG. 1A.

As shown, a first aqueous fluid 112 is flowed through channel segment 102 toward junction 110. A second fluid 114 that is immiscible with the first fluid 112 is flowed into junction 110 via each of channel segments 104 and 106, and into fourth channel segment 108. As the aqueous first fluid 112 reaches the junction 110, it is pinched by the flow of the second fluid 114 from channel segments 104 and 106, and individual droplets 116 of the aqueous first fluid 112 are dispensed into fourth channel segment 108. In some cases, a portion of the fourth channel segment 108 proximal to the junction 110 may be provided with a reduced cross-section (not shown) as compared to the junction and/or channel segments 102, 104 and 106 to facilitate droplet formation within the fourth channel segment 108.

As discussed in greater detail below, additional channel segments may be provided either upstream, downstream or both, of junction 110, in any of channel segments 102, 104, 106 or 108, to allow for the delivery of additional fluids into either the aqueous first fluid stream in segment 102, e.g., additional reagents, buffers, or the like, the partitioning fluid in segments 104 and/or 106, or the droplet containing stream in channel segment 108.

As will be appreciated, this basic channel architecture is widely useful in both generation of microcapsules for encapsulation of reagents, as well as in the ultimate partitioning of those encapsulated regents with other materials.

In one particular example and with reference to FIGS. 1A and 1B, above, a first aqueous solution of polymer precursor material may be transported along channel segment 102 into junction 110 as the aqueous fluid 112, while a second fluid 114 that is immiscible with the polymer precursor is delivered to the junction 110 from channel segments 104 and 106 to create discrete droplets of the polymer precursor material flowing into channel segment 108. In some aspects, this second fluid 114 comprises an oil, such as a fluorinated oil, that includes a fluorosurfactant for stabilizing the resulting droplets, e.g., inhibiting subsequent coalescence of the resulting droplets. Examples of particularly useful partitioning fluids and fluorosurfactants are described for example, in U.S. Patent Application No. 2010-0105112, the full disclosure of which is hereby incorporated herein by reference in its entirety for all purposes. Polymer precursor materials may include one or more of polymerizable monomers, linear polymers, or other In preparing gel microcapsules, an activation agent may also be combined with the aqueous stream 112 from channel 102. In some aspects, this activation agent is disposed within the second fluid streams 114 in one or more of channels 104 and 106, allowing for the simultaneous formation of droplets and commencement of a reaction to create the desired microcapsules 116. For example, in the case where the polymer precursor material comprises a linear polymer material, e.g., a linear polyacrylamide, PEG, or other linear polymeric material, the activation agent may comprise a cross-linking agent, or a chemical that activates a cross-linking agent within the first stream. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl)cystamine (BAC) comonomer, an agent such as tetraethylmethylenediamine (TEMED) may be provided within the second fluid streams in channel segments 104 and 106, which initiates the copolymerization of the acrylamide and BAC into a cross-linked polymer network or, hydrogel.

Upon contact of the second fluid stream 114 with the first fluid stream 112 at junction 110 in the formation of droplets, the TEMED may diffuse from the second fluid 114 into the aqueous first fluid 112 comprising the linear polyacrylamide, which will activate the crosslinking of the polyacrylamide within the droplets, resulting in the formation of the gel, e.g., hydrogel, microcapsules 116, as solid or semi-solid beads or particles.

Although described in terms of polyacrylamide encapsulation, other 'activatable' encapsulation compositions may also be employed in the context of the present disclosure. For example, formation of alginate droplets followed by exposure to divalent metal ions, e.g., Ca2+, can be used as an encapsulation process using the described processes. Likewise, agarose droplets may also be transformed into capsules through temperature based gelling, e.g., upon cooling, or the like.

In accordance with some aspects of the present disclosure one or more reagents may be associated with the microcapsule at the time of its formation. In particular, one or more reagents may be associated with a precursor reagent to the polymer matrix that makes up the microcapsule e.g., the linear polymer, such that the reagent(s) will be entrained within or otherwise associated with the formed microcapsule. For example, the reagent(s) may be coupled to a linear polymer material that is cross-linked into a microcapsule using the processes described herein, resulting in the reagents being coupled to the formed and cross-linked gel microcapsule. Alternatively, the reagent may be combined with the polymer precursor that includes active binding sites that interact with the reagent, either in the precursor stream or in the microcapsule after formation. In still other aspects, as with the cross-linking activation agent described elsewhere herein, an activator may also be contacted with the polymer precursor or formed microcapsule that activates sites on the polymer matrix of the microcapsule to which the reagent components may associate, covalently or non-covalently.

Reagents to be incorporated into the microcapsule may include any of a variety of different reagents or other components useful in the ultimate use of the microcapsule, e.g., an analytical reaction. Such reagents may include labeling groups (e.g., fluorescent dye molecules, FRET pairs, fluorescent nanoparticles, fluorescent proteins, mass labels, electrochemical labels or the like). These reagents may include biological or biochemical reagents, such as nucleic acids, nucleic acid analogues, nucleic acid mimetics, polynucleotides or analogues, oligonucleotides or analogues, enzymes, substrates, antibodies or antibody fragments, antigens, epitopes, receptors, and receptor binding components, proteins, polypeptides, amino acids, polysaccharides, or virtually any type of biochemical reagent useful in any of a wide variety of analyses. Likewise, compounds that act upon biological or biochemical systems are also envisioned for inclusion in such microcapsules, e.g., small molecule pharmaceutically active compounds, radiological compounds, inhibitors and or initiators of biological or biochemical compounds, chemical library compounds, or the like. In certain examples, these reagents may include any of a wide of variety of different reagents that are applicable to desired reactions to be carried out within the ultimately created partition, such as nucleic acid replication reagents (e.g., primers, polymerases, nucleotides or nucleotide analogues, buffers, co-factors, or the like), specific binding groups (e.g., receptors, antibodies or antibody fragments, binding peptides), or any other reagents (e.g., enzymes, substrates, catalysts/initiators, substrates, inhibitors, or the like).

In one example, a polynucleotide having an acrydite moiety is provided within the aqueous fluid, where the polynucleotide is coupled to the polymer precursor prior to its cross-linking into a bead as described herein. This polynucleotide may comprise one or more functional nucleic acid sequences, such as primer sequences, attachment sequences, ligation sequences or barcode sequences. See, e.g., U.S. Patent Application No. 61/937,344, which is entirely incorporated herein by reference.

Once created, the microcapsules may be collected, e.g., from a reservoir or other outlet at the end of channel segment 108. The collected microcapsules may then be washed to remove crosslinking agent, non-crosslinked polymer, emulsion oil and surfactant, any other non-coupled reagents, out-sized microcapsules or portions thereof, as well as any other contaminants imparted to the microcapsules during their creation that may potentially interfere with the use of the methods and systems described herein. In some aspects, the microcapsules will comprise substantially pure microcapsule compositions. By substantially pure microcapsule compositions is meant that the monodisperse populations of microcapsules, as described above, and their associated desired buffer and reagents will make up at least 90% of the composition, at least 95% of the composition, at least 99% of the composition, and in many cases at least 99.9% of the composition. Once washed, these microcapsules may be re-suspended in an aqueous solution, e.g., a buffer and/or one or more selected reagents, for use in subsequent processing. In accordance with the above, a variety of different wash protocols may be used in series or in the alternative in generating the substantially pure microcapsules described above. By way of example, in some cases, the wash may comprise a simple buffer exchange wash where the microcapsules are separated from their supporting liquid, e.g., through settling, centrifugation, filtration, or the like, and then re-suspended in a new buffer solution that may or may not be the same buffer as was originally containing the microcapsules. This type of wash may be repeated multiple times to remove free contaminants from the microcapsules. In alternative or additional wash steps, a more stringent washing process may be employed to remove certain bound species from the microcapsules. For example, where a microcapsule comprises nucleic acid, protein or other associated reagents, a denaturing wash step may be employed to remove additional bound excess proteins, nucleic acids or the like. For example, in some cases, the microcapsules may be washed with chaotropic agents, such as urea, at elevated temperatures to remove other non-covalently bound species, e.g., hybridized nucleic acids, etc. In still other aspects, wash steps may be combined with extractive techniques, in order to remove species that may be entrained within the interior of the microcapsules. For example, in some cases, these extractive processes may include electroelution, osmotic elution or other techniques to draw non-covalently bound species from within microcapsules.

In many cases, the substantially pure microcapsule compositions are substantially free from aggregated microcapsules, e.g., two, three, four or more microcapsules adhered together. Separation of aggregated microcapsules may be carried out through a variety of methods, including for example, size or flow based separation techniques, e.g., filtration.

Figure 1C:
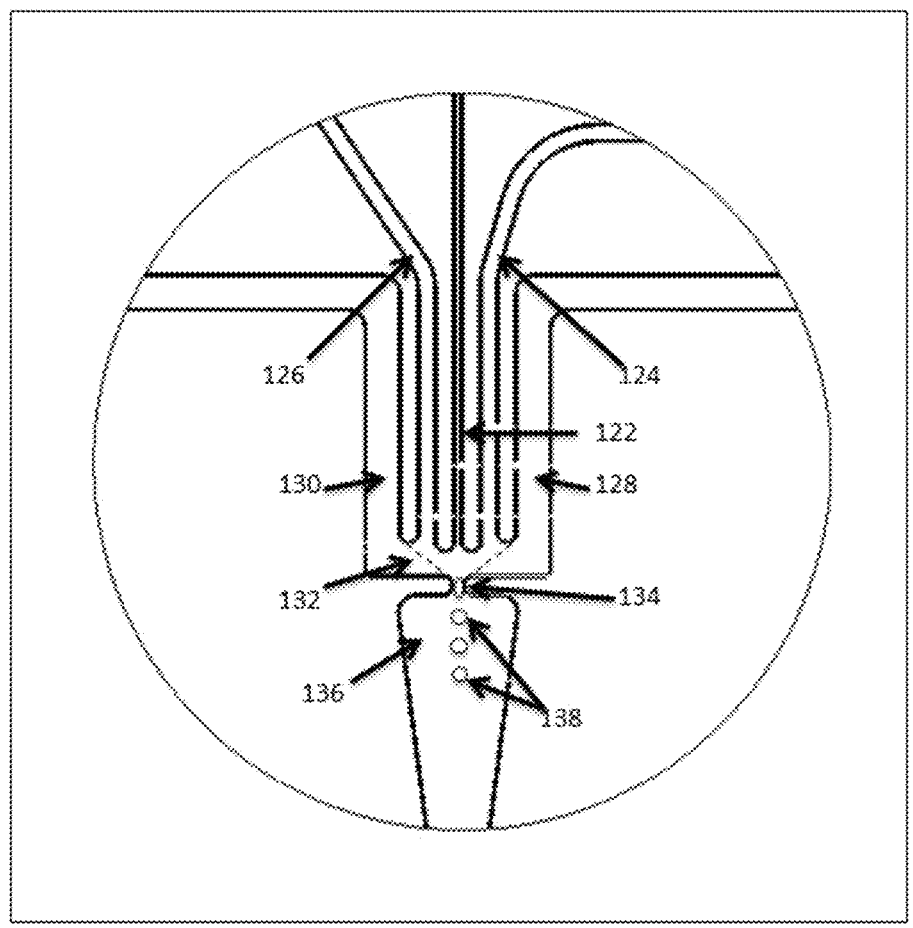

Although described with reference to the channel architecture shown in FIGS. 1A and 1B, it will be appreciated that variations of these structures and architectures may be practiced within the scope of the present disclosure. For example, in some cases, the interface of the aqueous stream with the partitioning fluid may differ from the specific architectures described above. In particular, as shown in FIG. 1A, the intersection of channel segment 112 with channel segments 104 and 106 provides an interface between the aqueous fluid flow in channel segment 102 and the partitioning fluid. The droplets are formed as the aqueous fluid is pushed into and through that interface into channel segment 108. In some cases, however, the interface may be presented within an open space or chamber or channel segment manifold within a fluidic device, such that the interface exists as a "wall" of partitioning fluid. An example of this type of droplet generation junction is illustrated in FIG. 1C. As shown, a first channel segment 122 is fluidly connected to a fluid manifold 132 that forms part of the droplet generation junction. The manifold 132 is structured as a larger open chamber, i.e., larger than the first channel segment, with a droplet dispensing channel 134 exiting the manifold through which formed droplets 138 are expelled through dispensing channel or aperture 134 into channel segment 136. In some cases, additional side channel segments 124 and 126 are also provided fluidly connected to the manifold 132, as are channel segments 128 and 130. In operation, a first aqueous fluid (e.g., the aqueous polymer precursor fluid as described with reference to FIG. 1B, or the microcapsule containing aqueous fluid described with reference to FIG. 3B, below) is flowed into the manifold 132. An immiscible fluid is introduced into the manifold through side channels 128 and 130. Within the manifold 132, the immiscible fluid forms an interface that traverses the manifold 132 to the droplet dispensing port (shown as the dashed lines extending from channel segments 128 and 130 to dispensing channel 134). In some cases, additional aqueous fluids are introduced into the manifold through side channels 124 and 126. As the fluids flow through the droplet dispensing channel 134, the aggregate aqueous fluids, i.e., that from channel segment 122 and in some cases from segments 124 and 126, are surrounded by the immiscible fluid from channel segments 128 and 130 and expelled through dispensing channel segment 134 into channel segment 136 as droplets 138 of aqueous fluids within an immiscible fluid emulsion. As will be appreciated, controlling the rate of droplet formation, as well as the relative volumes of fluids combined in droplets within these types of structures is accomplished through many of the same mechanisms described above for basic channel intersections. In particular, controlled flow may be achieved through a number of mechanisms, including, for example, controlling the flow rates of the fluids being introduced into the manifold, controlling the geometry of the channels as they enter the manifold 132, e.g., channel shape, dimensions (depth and/or width), intersection contours and structure, and setback from the manifold as compared to other channels.

Additionally, although illustrated in FIG. 1A as a single interface for droplet generation, it will be appreciated that the devices and systems of the present disclosure will typically comprise multiplexed droplet generating interfaces in order to increase the throughput at which one can produce droplets for microcapsule formation or for partitioning of microcapsules, as described elsewhere herein. For example, a device or system of the present disclosure may include multiple duplicate channel networks of the architectures shown in FIGS. 1A and/or 1C. Further, for such multiplexed devices or systems, some of the various channel segments within the duplicate channel networks may have common fluid sources in terms of a common reservoir or a common channel or channel manifold, or may feed to a common outlet or reservoir. Likewise, in the case of alternate architectures, multiple aqueous fluid feed channel segments may be provided in communication with the partitioning fluid chamber.

Figure 2:
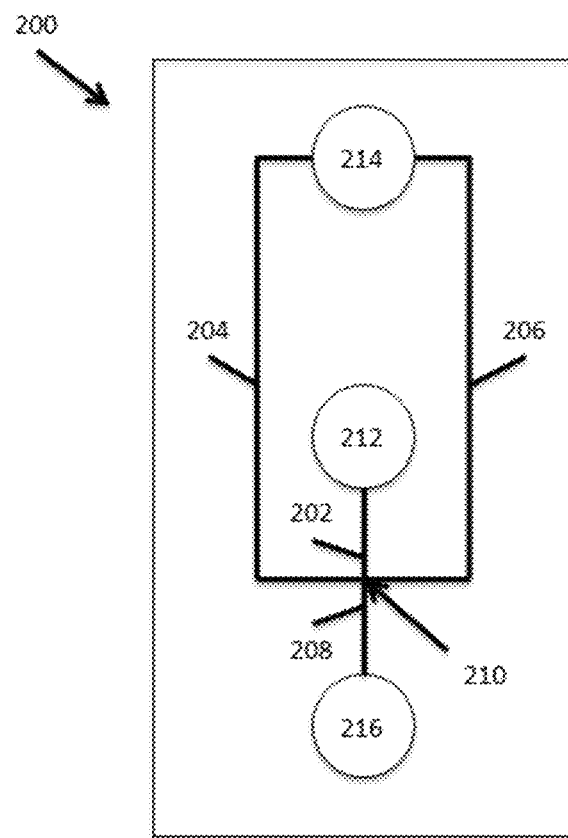
FIG. 2 schematically illustrates a simple, example fluidic channel architecture for partitioning microcapsules and other fluids into droplets in a water-in-oil emulsion.

FIG. 2 schematically illustrates a microfluidic device or device module for producing the microcapsules described above. As shown, the microfluidic device typically includes a body structure 200 that includes within its interior portion, a channel network that includes channels segments 202, 204, 206 and 208. These channel segments all communicate with a common channel junction 210. The device body structure also includes reagent reservoirs 212 and 214. As shown, reagent reservoir 212 is fluidly coupled to channel segment 202, while reagent reservoir 214 is fluidly coupled to channel segments 204 and 206. A third outlet reservoir is shown as reservoir 216, which is provided in fluid communication with channel segment 208. As will be appreciated, the aqueous polymer gel precursor may be provided in reservoir 212, while the partitioning fluid and activating agent are provided in reservoir 214. Flow of these fluids through junction 210, creates the microcapsules as described above, which flow into and are harvested from reservoir 216.

These microfluidic devices or device modules may be fabricated in any of a variety of conventional ways. For example, in some cases the devices comprise layered structures, where a first layer includes a planar surface into which is disposed a series if channels or grooves that correspond to the channel network in the finished device. A second layer includes a planar surface on one side, and a series of reservoirs defined on the opposing surface, where the reservoirs communicate as passages through to the planar layer, such that when the planar surface of the second layer is mated with the planar surface of the first layer, the reservoirs defined in the second layer are positioned in fluid communication with the termini of the channel segments on the first layer. Alternatively, both the reservoirs and the connected channel structures may be fabricated into a single part, where the reservoirs are provided upon a first surface of the structure, with the apertures of the reservoirs extending through to the opposing surface of the structure. The channel network is fabricated as a series of grooves and features in this second surface. A thin laminating layer is then provided over the second surface to seal, and provide the final wall of the channel network, and the bottom surface of the reservoirs.

These layered structures may be fabricated in whole or in part from polymeric materials, such as polyethylene or polyethylene derivatives, such as cyclic olefin copolymers (COC), polymethylmethacrylate (PMMA), polydimethylsiloxane (PDMS), polycarbonate, polystyrene, polypropylene, or the like, or they may be fabricated in whole or in part from inorganic materials, such as silicon, or other silica based materials, e.g., glass, quartz, fused silica, borosilicate glass, or the like.

Polymeric device components may be fabricated using any of a number of processes including embossing techniques, micromachining, e.g., laser machining, or in some aspects injection molding of the layer components that include the defined channel structures as well as other structures, e.g., reservoirs, integrated functional components, etc. In some aspects, the structure comprising the reservoirs and channel structures may be fabricated using, e.g., injection molding techniques to produce polymeric structures. In such cases, a laminating layer may be adhered to the molded structured part through readily available methods, including thermal lamination, solvent based lamination, sonic welding, or the like.

As will be appreciated, structures comprised of inorganic materials also may be fabricated using known techniques. For example, channel and other structures may be micromachined into surfaces or etched into the surfaces using standard photolithographic techniques. In some aspects, the microfluidic devices or components thereof may be fabricated using three-dimensional printing techniques to fabricate the channel or other structures of the devices and/or their discrete components.

As noted previously, the above-described channel architectures may also be readily employed in the partitioning of the above described microcapsules, e.g., comprising the encapsulated reagents, within droplets created in an immiscible fluid, such as in a "water-in-oil" (WO) emulsion system, where an aqueous solution, and particularly, an aqueous solution that includes the encapsulated reagents described herein, is dispersed as partitioned droplets within an immiscible dispersion or partitioning fluid, such as an immiscible oil.

FIG. 3 schematically illustrates the partitioning of encapsulated reagents. As shown, and with reference to the fluidic architecture shown in FIG. 1A, a first aqueous fluid that includes the beads encapsulating at least a first reagent is flowed through channel segment 102 into channel junction 110. The dispersion fluid is flowed into junction 110 from side channel segments 104 and 106. The aqueous fluid is then partitioned into droplets within the flowing stream of dispersion fluid, with individual droplets including the encapsulated reagents, and in some cases, containing only a single reagent bead or capsule.

Figure 3A:
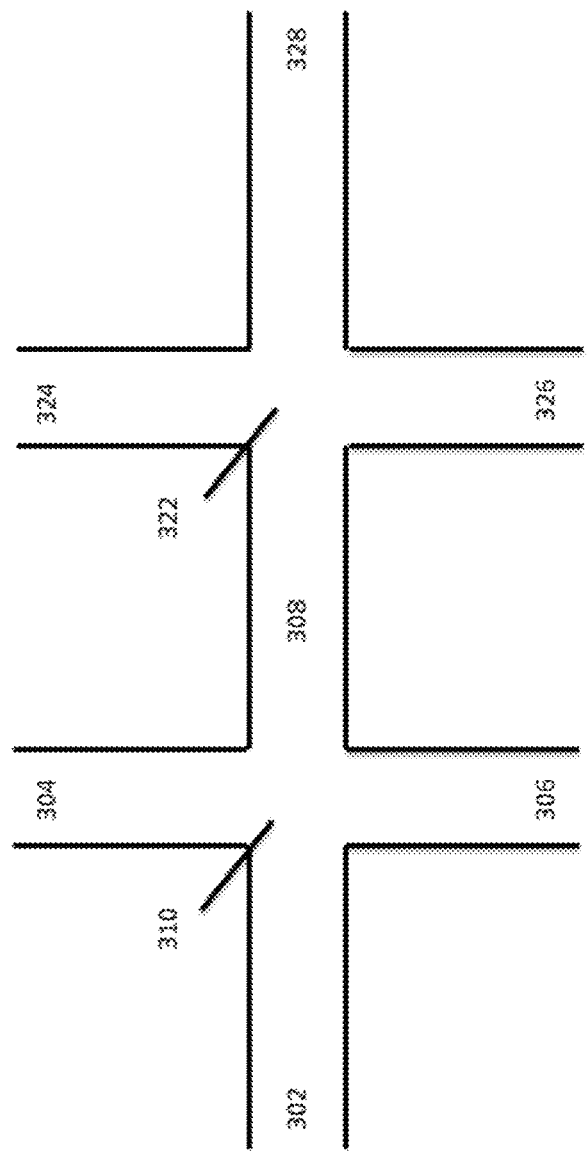
FIGS. 3A and 3B schematically illustrate an example fluid channel architecture for partitioning encapsulated reagents into droplets in an emulsion.

The above-described channel architecture is included within an example of a channel system shown in FIG. 3A, for partitioning microcapsules, including, e.g., encapsulated reagents, with sample materials into, for example, a water-in-oil emulsion system. As shown, a first channel segment 302 is shown fluidly connected to channel segments 304, 306 and 308 at first channel junction 310. Fourth channel segment 308 fluidly connects first channel junction 310 to second channel junction 322 that is also fluidly coupled to channel segments 324, 326 and 328.

Figure 3B:
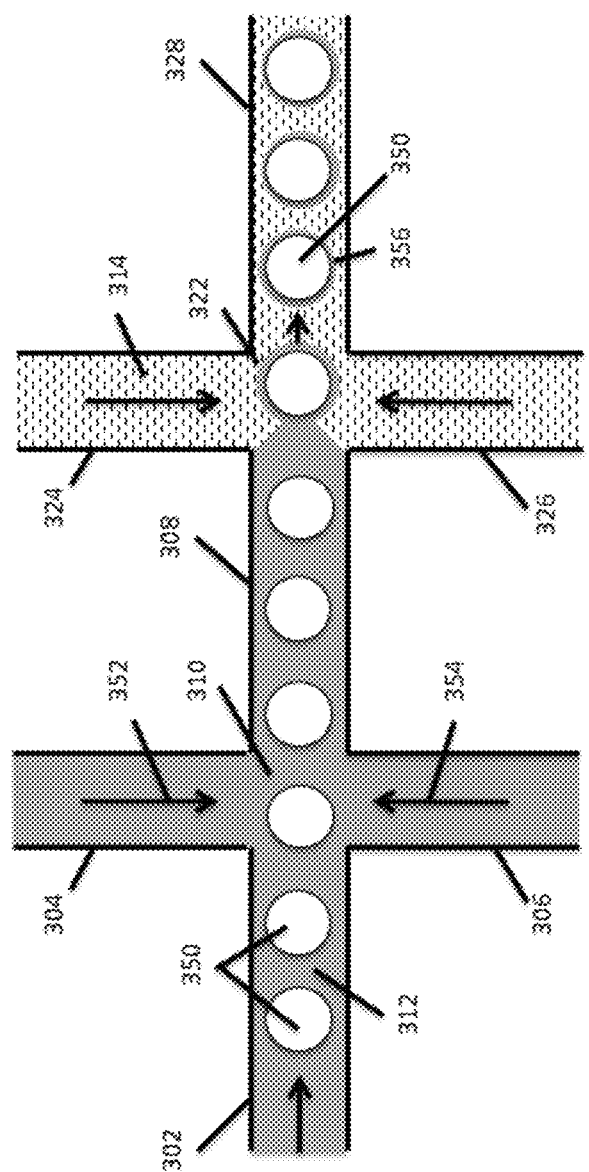

In the context of partitioning encapsulated reagents, the channel system of FIG. 3A is shown in FIG. 3B. As shown, a first stream of a first aqueous fluid 312 containing microcapsules 350 (e.g., such as microcapsules prepared as described above), beads or the like, that may include encapsulated reagents, are flowed through channel segment 302 into channel junction 310. Additional streams of second aqueous fluids 352 and 354 are introduced into channel junction 310 from channel segments 304 and 306 to join the first aqueous fluid 312 containing the microcapsules 350. The aqueous fluids added through each of channel segments 304 and 306 may be the same as or different from each other and the fluid portion of aqueous stream 312. As will be appreciated, the various channel segments will typically be fluidly coupled to sources of the fluids that are to be flowed through those channel segments. Such fluid sources may include reservoirs integrated within a device or interfaced with a device, or may include other interfaces with other fluidic systems, e.g., syringes, pumps, fluidic networks or the like, or interfaced with external reservoirs, e.g., external fluid accession systems for drawing fluids from tubes, vials, wells, or the like, or even external processing systems, e.g., amplification systems, sample material extraction systems, filtration systems, separation systems, liquid chromatography systems, or the like.

In some aspects, the additional aqueous fluids added through side channels 304 and 306 may include sample materials that are to be partitioned along with the encapsulated reagents included within the microcapsules. For example, the second aqueous fluid may include sample nucleic acids that may be partitioned into separate droplets along with the reagents included with the microcapsules, such as barcode sequences, functional sequences and the like. Additional reagents may also be added in the second aqueous fluids. In some cases, e.g., where the encapsulated reagents are to be employed in nucleic acid replication or synthesis reactions, the additional fluids may include reagents for such reactions, such as DNA polymerase enzyme(s), primer sequences, nucleotides or nucleotide analogues, reaction co-factors, buffers and the like, as well as any of a variety of other reagents, e.g., dyes, labels, chelators, inhibitors, initiators, substrates, etc.

In some cases, the reagents that are added may include reagents that stimulate release of the encapsulated reagents into the resulting droplets. For example, in some cases, the reagents may be associated with the microcapsule through a disulfide linkage or other chemically cleavable linkage, or the microcapsules may be structurally held together by disulfide crosslinking, or other chemically cleavable cross-linkers. As such, addition of a reducing agent, such as dithiothreitol (DTT) can result in the eventual release of the reagents on the microcapsules, either through direct release or through dissolution of the microcapsule, or both (See, e.g., U.S. Patent Application No. 61/940,318, filed Feb. 14, 2014, the full disclosure of which is incorporated herein by reference in its entirety for all purposes). Alternatively or additionally, other cleavable linkages may be used to crosslink microcapsules. Examples of such linkages include, e.g., photocleavable or chemically cleavable linkages or cross-linkers.

The combined aqueous stream, e.g., from fluids 312, 352 and 354, flows through channel segment 308 into channel junction 322. A third fluid 314 that is immiscible with the combined aqueous stream flowing from channel segment 308 is introduced into channel junction 312 from each of channel segments 324 and 326 to form droplets 356 that include the microcapsules 350, as well as some amount of the combined aqueous fluids. In many cases, this third, immiscible fluid includes an oil, such as a fluorinated oil containing a fluorosurfactant, as described above that is suitable for forming water-in-oil emulsions with stabilized resulting droplets. Other suitable emulsion systems may in some cases include silicon and hydrocarbon oil/surfactant systems.

As alluded to above, the devices described herein are useful in providing the microcapsules within aqueous droplets in an immiscible fluid. As will be appreciated, in a number of applications, it is particularly beneficial to provide a desired level of microcapsule occupancy in created partitions. In general, this is accomplished by controlling the combination of the aqueous stream that includes the microcapsule, and the streams of the immiscible fluid, such that the probability of more than the desired number of microcapsules being incorporated into a given partition is acceptably low. This may generally be accomplished through control of the flow of microcapsules, along with the flow of the other fluids coming together in the partitioning zone, e.g., junction 322 in FIG. 3, can be controlled so as to substantially provide for a desired number of microcapsules per partition.

In many cases, the devices, systems and methods are used to ensure that the substantial majority of occupied partitions (e.g., partitions containing one or more microcapsules) will include no more than 1 microcapsule per occupied partition. In particular, in some cases, the partitioning process is controlled such that fewer than 50% of the occupied partitions contain more than one microcapsule, fewer than 45% of the occupied partitions contain more than one microcapsule, fewer than 40% of the occupied partitions contain more than one microcapsule, fewer than 35% of the occupied partitions contain more than one microcapsule, fewer than 30% of the occupied partitions contain more than one microcapsule, fewer than 25% of the occupied partitions contain more than one microcapsule, and in many cases, fewer than 20% of the occupied partitions have more than one microcapsule, while in some cases, fewer than 10% or even fewer than 5% of the occupied partitions will include more than one microcapsule per partition. Accordingly, in many cases, the resulting partitions will result in at least 50% of the partitions containing one and only one microcapsule (i.e., a single microcapsule), at least 55% of the partitions containing one and only one microcapsule, at least 60% of the partitions containing one and only one microcapsule, at least 65% of the partitions containing one and only one microcapsule, at least 70% of the partitions containing one and only one microcapsule, at least 75% of the partitions containing one and only one microcapsule, at least 80% of the partitions containing one and only one microcapsule, at least 80% of the partitions containing one and only one microcapsule, at least 85% of the partitions containing one and only one microcapsule at least 90% of the partitions containing one and only one microcapsule, and in some cases at least 95% of the partitions containing one and only one microcapsule.

Additionally or alternatively, in many cases, it is desirable to avoid the creation of excessive numbers of empty partitions. While this may be accomplished by providing sufficient numbers of microcapsules into the partitioning zone, the poissonian distribution can expectedly increase the number of partitions that can include multiple microcapsules. As such, in accordance with aspects of the present disclosure, the flow of one or more of the microcapsules, or other fluids directed into the partitioning zone are controlled such that, in many cases, no more than 50% of the generated partitions will be unoccupied, i.e., including less than 1 microcapsule, no more than 25% of the generated partitions, or no more than 10% of the generated partitions, will be unoccupied. Further, in some aspects, these flows are controlled so as to present non-poissonian distribution of single occupied partitions while providing lower levels of unoccupied partitions. Restated, in some aspects, the above noted ranges of unoccupied partitions will be achieved while still providing any of the above-described single occupancy rates described above. For example, in many cases, the use of the devices, systems and methods of the present disclosure creates resulting partitions that have multiple occupancy rates of from less than 25%, less than 20%, less than 15%, less than 10%, and in many cases, less than 5%, while having unoccupied partitions of from less than 50%, less than 40%, less than 30%, less than 20%, less than 10%, and in some cases, less than 5%. Methods, systems and device configurations for controlling the various flows within the channel networks are described in greater detail below.

Although described in terms of providing substantially singly occupied partitions, above, in certain cases, it is desirable to provide multiply occupied partitions, e.g., containing two, three, four or more microcapsules within a single partition. Accordingly, as noted above, the flow characteristics of the microcapsule containing fluids and partitioning fluids may be controlled to provide for such multiply occupied partitions. In particular, the flow parameters may be controlled to provide a desired occupancy rate at greater than 50% of the partitions, greater than 75%, and in some case greater than 80%, 90%, 95%, or higher.

Additionally, in many cases, the multiple microcapsules within a single partition may comprise different reagents encapsulated therein. In such cases, it may be advantageous to introduce different microcapsules into a common channel or droplet generation junction, from different microcapsule sources, i.e., containing different encapsulated reagents, through different channel inlets into such common channel or droplet generation junction. In such cases, the flow and frequency of the different microcapsules into the channel or junction may be controlled to provide for the desired ratio of microcapsules from each source, while ensuring the desired pairing or combination of such microcapsules into a partition.

Although shown with two junctions and their associated channel segments, it will be understood that additional channels may be provided within the devices of the present disclosure to deliver additional components to the various fluids, capsules and partitions described above. These additional channels may be provided intersecting any of the various channel segments described herein for addition of a variety of components to any one or more of the various fluids flowing within those channel segments at different positions and for different purposes. For example, in one aspect, one or more additional side channels may be provided intersecting the channel segment 328, described above, for the purpose of introducing new fluids, reagents, or additional partitioning fluids into partitioned fluids within the channel segment 328.

Likewise, additional channel segments may be provided intersecting channel segments 302 and/or 308, in order to introduce additional fluids into the aqueous stream prior to separating that fluid stream into droplets with the partitioning fluid. Additionally, still other channel segments can be provided intersecting any of the side channel segments, e.g., channel segments 304, 306, 324, or 326, in order to deliver different fluids into those channels. Such systems can allow the alteration of fluids being introduced into the partitioning stream in real time by controlling which fluids are provided through the respective side channels, e.g., allowing one to change reactants, change the partition fluid characteristics, or any of a variety of other conditions.

In some cases, these additional fluids may be for purposes of stimulating different reactions within the partitions by introducing new reagents to the partitions. For example, these additional fluids may provide one or more activating agents to the partitions or capsules, that cause the initiation of one or more reactions at any stage prior to or following partitioning.

Such activating agents may take any of a number different forms. For example, these activation reagents may cause the release of a reagent within a partition or capsule, to make it available for reaction, e.g., by cleaving a linkage between a microcapsule and the reagent, or by stimulating the disintegration of the microcapsule and subsequent reagent release. Alternatively or additionally, the activation reagent may comprise an initiator for a desired reaction, such as a missing critical reagent for the desired reaction, or the like. By way of example and for purposes of illustration, in cases where the desired reaction includes a nucleic acid polymerase mediated nucleic acid replication, an activation reagent may include a key missing reagent, such as one or more nucleoside triphosphates otherwise lacking from the mixture, a primer sequence, or one or more reaction co-factors suitable for a polymerase reaction, e.g., divalent metal ions like magnesium or manganese. In many cases, the use of such missing systems or activatable reagent systems for purposes of controlled initiation of a given reaction are referred to as "hot start" reagents, which are, as a general class, useful in conjunction with the systems of the present disclosure.

The activation reagents may alternatively or additionally initiate reactions on the partitions or capsules themselves or both, for example, disrupting the capsules or releasing reagents from those capsules, stabilizing or destabilizing partitions, e.g., to reduce or promote coalescence, respectively. A variety of reagent systems may be employed in the disruption of or release of reagents from the microcapsules of the present disclosure. These include the use of chemical stimuli described above, for cleaving chemical cross-linking or molecular attachment, as discussed in U.S. Patent Publication No. 2014/0378345, which is entirely incorporated herein by reference.

Figure 4:
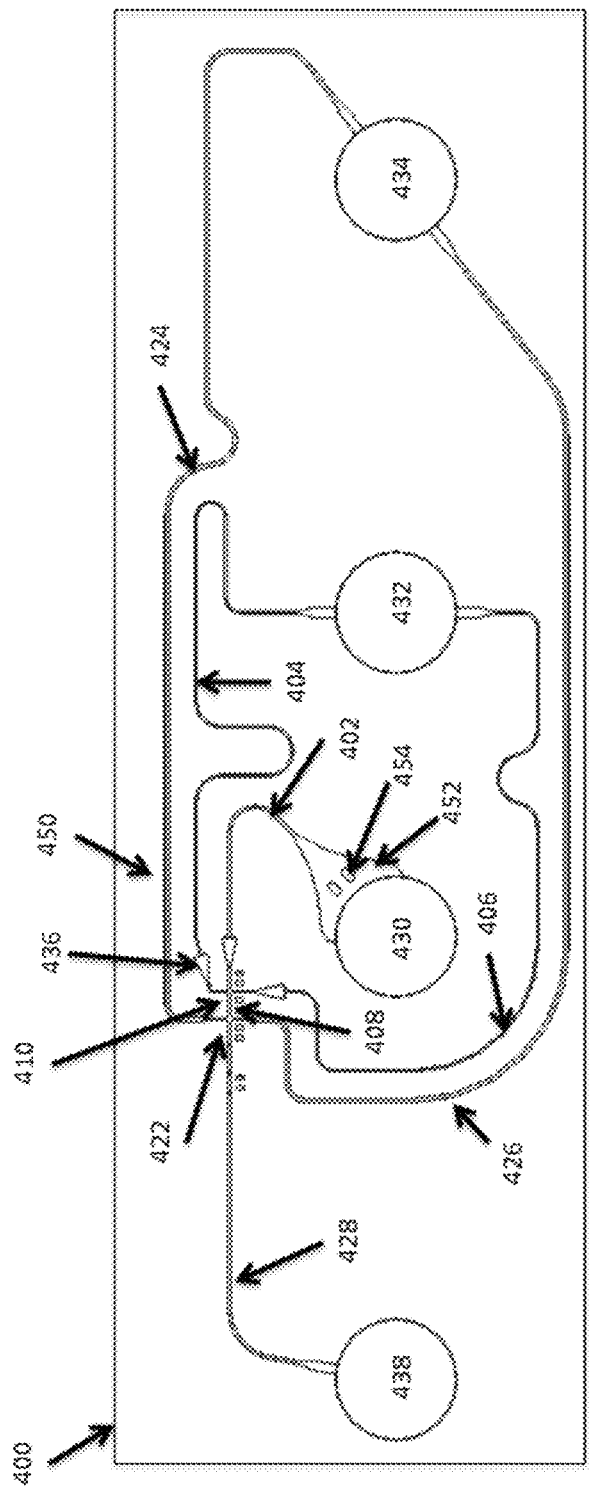
FIG. 4 schematically illustrates an example channel network and microfluidic device useful in partitioning encapsulated reagents.

FIG. 4 provides a schematic illustration of an overall exemplary microfluidic device or device module for partitioning encapsulated reagents as described above. As shown in FIG. 4, the overall device 400 provides one or more channel network modules 450 for generating partitioned microcapsule compositions. As shown, the channel network module 450 includes a basic architecture similar to that shown in FIG. 3B, above. In particular, the illustrated channel network module includes a first channel junction 410 linking channel segments 402, 404 and 406, as well as channel segment 408 that links first junction 410 to second channel junction 422. Also linked to second junction 422 are channel segments 424, 426 and 428.

As illustrated, channel segment 402 is also fluidly coupled to reservoir 430 that provides, for example, a source of microcapsules that may include one or more encapsulated reagents, suspended in an aqueous solution. Each of channel segments 404 and 406 are similarly fluidly coupled to fluid reservoir 432, which may provide for example, a source of sample material as well as other reagents to be partitioned along with the microcapsules. As noted previously, although illustrated as both channel segments 404 and 406 being coupled to the same reservoir 432, these channel segments may be coupled to different reservoirs for introducing different reagents or materials to be partitioned along with the microcapsules.

Each of channel segments 402, 404 and 406 may be provided with additional fluid control structures, such as passive fluid valve 436. These valves may provide for controlled filling of the overall devices by breaking the capillary forces that draw the aqueous fluids into the device at the point of widening of the channel segment in the valve structure. Briefly, aqueous fluids are introduced first into the device in reservoirs 430 and 432, at which point these fluids will be drawn by capillary action into their respective channel segments. Upon reaching the valve structure, the widened channel will break the capillary forces, and fluid flow will stop until acted upon by outside forces, e.g., positive or negative pressures, driving the fluid into and through the valve structure. Although illustrated as a widening of the channel in the width dimension, it will be appreciated that a passive valve structure may include a step up in any one or more cross-sectional dimensions of a channel region. For example, a passive valve may increase an increased stepped depth of a channel at the valve region. Again, when the fluid reaches the increased cross sectioned channel segment, the capillary forces will retain the fluid within the shallower channel. Again, as noted, the increase in cross-sectional dimension can be in any one or more cross-sectional dimensions, and may be increases in cross section of at least about 5%, 10%, 20%, 30%, 40%, 50%, 60%, 70%, 80%, 90% 100%, or even more. In many cases, it may be between about 5% and about 100% larger cross section, between about 5% and about 50%, between about 5% and about 20% of an increase in cross section. Although illustrated at a particular channel location, it will also be appreciated that these valve structures may be positioned along any channel location within a microfluidic channel network, including at an intersection of two or more channel segments, or within a singular channel.

Also shown in channel segment 402 is a microcapsule funneling structure 452, that both allows the efficient gathering of microcapsules from reservoir 430, regulation of microcapsule flow (as described in greater detail elsewhere herein), as well as reduced system failure due to channel clogging. As also shown, in some cases, the connection of channel segment 402 with reservoir 430, as well as the junctions of one or more or all of the channel segments and their respective reservoirs, may be provided with additional functional elements, such as filtering structures 454, e.g., pillars, posts, tortuous fluid paths, or other obstructive structures to prevent unwanted particulate matter from entering or proceeding through the channel segments.

Junction 410 is fluidly coupled to second junction 422. Also coupled to channel junction 422 are channel segments 424 and 426 that are, in turn fluidly coupled to reservoir 438, which may provide, for example, partitioning fluid that is immiscible with the aqueous fluids flowing from junction 410. Again, channel segments 424 and 426 are illustrated as being coupled to the same reservoir 438, although they may be coupled to different reservoirs, e.g., where each channel segment is desired to deliver a different composition to junction 422, e.g., partitioning fluids having different make up, including differing reagents, or the like.

In exemplary operation, microcapsules provided in reservoir 430 are flowed through channel segment 402 into first channel junction 410. The microcapsules will flow through valve 436, which, in addition to providing a passive fluid valve structure also operates as a microcapsule flow regulator, as described in greater detail below. The microcapsule flow regulator ensures more regular flow of microcapsules into and through junction 410 into channel segment 408. Within junction 410, the aqueous microcapsule solution is contacted with the aqueous fluids from reservoir 432, as introduced by channel segments 404 and 406. Due to laminar flow characteristics of the microfluidic channel networks, and without being bound to any particular theory of operation, aqueous fluids from channel segments 404 and 406 can ensheath the microcapsule composition with a second aqueous fluid layer, where the primary interaction between the two fluids is through simple diffusion, i.e., with a substantial lack of convective mixing.

The aqueous fluid stream is then flowed through channel segment 408 into second junction 422. Within channel junction 422, the aqueous fluid stream, including the regularly spaced flowing microcapsules, flowing through channel segment 408, is formed into droplets within the immiscible partitioning fluid introduced from channel segments 424 and 426. In some cases, one or both of the partitioning junction, e.g., junction 422 and one or more of the channel segments coupled to that junction, e.g., channel segments 408, 424, 426 and 428, may be further configured to optimize the partitioning process at the junction.

Further, although illustrated as a cross channel intersection at which aqueous fluids are flowed through channel segment 408 into the partitioning junction 422 to be partitioned by the immiscible fluids from channel segments 424 and 426, and flowed into channel segment 428, as described elsewhere herein, partitioning structure within a microfluidic device of the present disclosure may comprise a number of different structures.

As described in greater detail elsewhere herein, the flow of the microcapsules into junction 422, and in some cases the rate of flow of the other aqueous fluids and/or partitioning fluid through each of junctions 410 and 422, are controlled to provide for a desired level of partitioning of microcapsules, e.g., to control the number of microcapsules that will be partitioned in each droplet, the amount of reagents in each droplet, and control the overall operation of the device, e.g., to prevent clogging or other disruption, or the like.

Once the microcapsules are partitioned, they are flowed through channel segment 428 and into a recovery structure or zone where they may be readily harvested. As shown, the recovery zone includes, e.g., outlet reservoir 438. Alternatively, the recovery zone may include any of a number of different interfaces, including fluidic interfaces with tubes, wells, additional fluidic networks, or the like. In some cases, where the recovery zone comprises an outlet reservoir, the outlet reservoir will be structured to have a volume that is greater than the expected volume of fluids flowing into that reservoir. In its simplest sense, the outlet reservoir may, in some cases, have a volume capacity that is equal to or greater than the combined volume of the input reservoirs for the system, e.g., reservoirs 430, 432 and 434.

As will be appreciated, a single microfluidic device may include multiple substantially identical channel network modules that may each have self-contained fluid sources or may share one or more fluid reservoirs. For example, a single multiplexed device including multiple channel network modules may include a single source of one or more of the partitioning fluid, the microcapsule containing fluid, one or more reagent fluids, as well as sample fluids. As such, the multiple channel modules can be used to generate large amounts of the same type of partitioned microcapsules, e.g., by providing the same allocation of fluids in the corresponding reservoirs of each module 450 in a multiplexed device. In certain aspects, however, different channel network modules will be used in the generation of different partitioned microcapsules. Such different partitioned compositions may include different sample materials being allocated to the partitioned microcapsules, different initial microcapsules being allocated to the same or different sample materials, or application of different reagents to different to the same or different sample materials and/or different microcapsules. As noted above, where the same fluids are being introduced into the channel segments of different modules, it can be efficient to have such channel segments fluidly coupled to the same reservoir(s). These channel segments may be the same corresponding channel segments in each module or, depending upon the desired use, they may be different channel segments in different modules.

As will be appreciated, the rates at which different fluids are brought together in the channel structures described above can have an impact on the generation of the droplets whether for the purpose of microcapsule generation or for their subsequent separation into discrete partitions or droplets. Accordingly, in certain aspects, the devices used in the present disclosure provide for control of the various fluid flows within the integrated channel networks. Control of fluid flows within channel networks may be accomplished through a variety of mechanisms. For example, pressures may be applied at the origin of different channel segments, e.g., on reservoirs, in order to control fluid flow within that channel segment. By utilizing a pressure based flow, one may be able to independently control flows within different channel segments by coupling independently controlled pressure sources to the different channel segments to apply differential pressure gradients across each channel segment. In such cases, flow rates within different channel segments may be monitored, e.g., through interfaced detection systems, such as optical detectors, to provide feedback on the flow control aspects to allow modulation of flow.

Alternatively, a single pressure source may be coupled to all channel segments simultaneously, e.g., by coupling a pressure source to a manifold that simultaneously connects to the various channel segment origins or reservoirs. Where a single pressure is applied over multiple channels, the flow rates within those channels will be controlled by the level of resistance within each channel that is subject to fluid viscosity and channel dimensions (cross-section and length). In such cases, flow control is achieved by providing channel segments with the appropriate dimensions to achieve the desired flow rate given the viscosity of the fluids passing through it. By way of example, in order to achieve equivalent flow rates, channels used to flow more viscous fluids may be provided with wider and/or shorter channel segments than channels used to transport lower viscosity fluids.

Although described as a pressure source applied to channel origins, in some aspects, the pressure source may include a vacuum (or negative pressure) source that is applied to one or more of the outlet ports for a channel network, e.g., a terminal reservoir, i.e., reservoir 444 in FIG. 4. Application of a vacuum provides a number of advantages over positive pressure driven systems, including, e.g., provision of a single point of connection to an integrated channel network at the outlet vs. several inlet points, lack of microcapsule compression that may lead to channel inlet clogging in positive pressure systems, and the like.

In some cases, for the partitioning of microcapsules, the vacuum source may be applied to a node on an outlet channel segment that is distinct from the zone at which the partitioned microcapsules may be harvested. In particular, where a vacuum source is applied at the terminal reservoir, e.g., reservoir 438 in FIG. 4, the source can be disconnected from the reservoir in order to harvest the partitioned microcapsules from the terminal reservoir. In some cases, by separating the vacuum source interface node with the channel segment from the zone where partitioned microcapsules are harvested, one can obviate the need for disconnecting the vacuum source and improving the ease of use. In some cases, the vacuum interface node may include a terminal reservoir, e.g., reservoir 438, which may be configured with an interface component for interfacing with an integrated or discrete partition harvesting zone that allows harvesting of the partitions without removing the connected vacuum source. These and other interface components are described in detail below.

III. Additional Improved Microfluidic System Components

The precise handling and manipulation of microcapsules, either in their creation, or in their subsequent partitioning, creates a number of new challenges in microfluidic systems that are addressed by aspects of the present disclosure. In particular, flow of microcapsule in fluidic and especially microfluidic systems can be subject to certain variabilities many of which have been alluded to above, including varied flow rates or dispensing frequencies, channel clogging, variable partitioning, sampling or dispensing biases, or the like. This disclosure provides numerous improved components, devices, methods and systems for addressing many of these issues.

For example, in certain aspects, the present disclosure addresses, e.g., sampling biases or variability from microcapsules in a reservoir. In particular, in some cases, one or more reservoirs into which microcapsules are deposited in a system or device described herein, e.g., reservoir 430 shown in FIG. 4, are configured to improve the flow of microcapsules into their connected channel segments.

Figure 5:
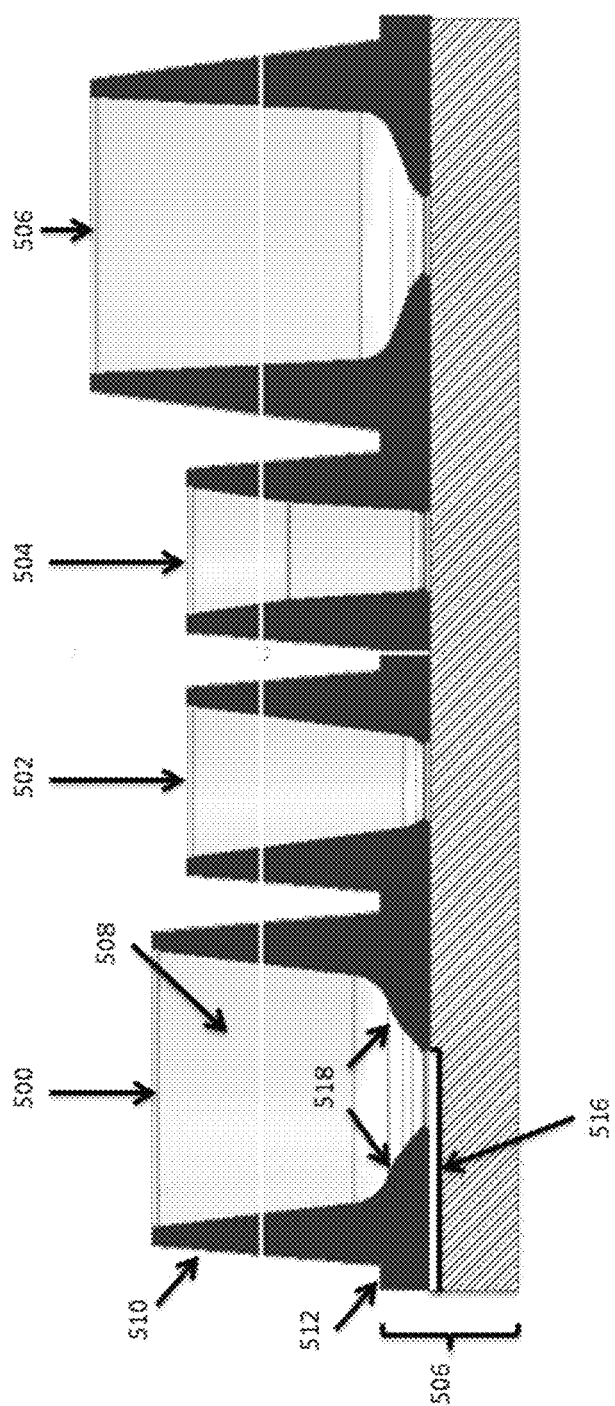
FIG. 5 schematically illustrates a side view of an example reservoir structure for enhancing manipulation of microcapsule compositions within fluidic devices.

In one example, the reservoirs that are used to provide the microcapsules or other reagents may be provided with a conical bottom surface to allow for funneling of the microcapsules toward the inlets for the channel segments connected to the reservoirs. This is schematically illustrated in FIG. 5A, which shows an example of reservoirs 500, 502, 504 and 506, viewed from the side. As shown, the reservoir 500 includes side walls 510 that extend from an upper surface 512 of a microfluidic device 506. An interior cavity portion 508 of the reservoir extends into the microfluidic device 506 and is provided in communication with a fluidic channel 516. As shown, cavity portion 508 possesses a tapering or conical shape toward the inlet of channel 516, as defined by narrowing of the cavity 508, by virtue of converging sidewalls 518 of cavity 508.

In additional aspects, microcapsule loading into channel segments may be enhanced through the inclusion of a broadened interface region, or inlet, between the reservoir and the connected fluid channel. One example of this is illustrated in the channel network of FIG. 4, where the interface of channel segment 402 with reservoir 430 is provided with funneling channel structure 452, that both enhances the introduction of microcapsules into the channel segment, as well as provides some flow regulating characteristics for the microcapsules into the channel segment. Also shown, are obstructive structures 454, that provide barriers for larger particulate matter that may be a contaminant within the reservoir and may impair the flow of fluids through the channels of the device. As will be appreciated, the various reservoirs may each or all include filtration or particle blocking elements within them that mat be the same or different, depending upon the fluids to be disposed in the reservoir. For example, in some cases, while a simple structural barrier, like the pillar structures shown in FIG. 4 (e.g., structures 454) may be used in the channel interfaces with the microcapsule containing reservoirs, for those reservoirs containing aqueous solutions, e.g., sample materials or reagents, more or less stringent filtration components may be integrated therein, e.g., at the bottom of a reservoir, in order to filter the contents of the reservoir, in situ, to a greater or lesser degree. A variety of filtration media, including, e.g., membrane filters, frits, or other known filter types, can be readily incorporated into the reservoirs within the devices of the present disclosure.

Similar to the broadened interfaces described above, the interfaces may include multiple discrete channel inlets from a given reservoir, to ensure that the flow of microcapsules into and through the channel segments is less susceptible to interruption or clogging, as well as to ensure that microcapsules disposed in the reservoir are accessed at multiple points, rather than at a single point or channel inlet. In particular, for a given reservoir, there may be provided a plurality of channel inlets that fluidly connect the reservoir to a single channel segment (or flow regulating junction, as described in greater detail below) within the microfluidic device. Further, as described above, the multiple channel inlets may be provided with one or more of the functional elements described previously, e.g., funneling structures, filtering elements such as pillars, posts or tortuous paths, or the like.

As noted in the discussion of the microcapsule partitioning above, the flow of microcapsules, along with the flow of the other fluids coming together in the partitioning zone, e.g., junction 322 in FIG. 3, can be controlled so as to substantially provide for a desired number of microcapsules per partition. In many cases, the substantial majority of occupied partitions (e.g., partitions containing one or more microcapsules) will include no more than 1 microcapsule per occupied partition, while in some cases also reducing the number of unoccupied partitions created.

As described above, the methods, devices and systems of the present disclosure generally accomplish a desired level of allocation of microcapsules to partitions through the controlled combination of the microcapsules and partitioning or dispersion fluid into droplets, e.g., through controlling the flow rates of microcapsules and oil in to the droplet generating junction of a microfluidic device, i.e., junction 312 as shown in FIG. 3.

Flowing of microcapsules from reservoirs through channels and into channel junctions can be subject to a great deal of variability, as these microcapsules may flow at a that is defined by the happenstance of when the microcapsule enters a channel segment, and its flow rate through that channel segment. Accordingly, in certain aspects, the microfluidic systems of the present disclosure may include microcapsule flow regulator components within the appropriate channel segment to provide such microcapsules flowing into the droplet forming region at a more defined regularity.

The microcapsule flow regulators included within the channel systems described herein will typically provide microcapsules flowing within channels at a relatively regular frequency. In particular, during a given timeframe in which droplets are being generated, e.g., a 10 second window, a 30 second window, a one minute window, a 2 minute window, a 3 minute window, or over the steady state operation of an entire droplet generation run (e.g., not including start up and shut down), the frequency at which these microcapsules are flowing will typically have a coefficient of variation of less than 50%, less than 40%, less than 30%, less than 20%, less than 10%, and in some cases, less than 5%. As will be appreciated, the flow frequency of microcapsules reflects the number of microcapsules that flow past a given point in a conduit within a one second period of time. Frequency measurements may typically be based upon sub-second or one second intervals, but may also be based upon multiple second, multiple minute or longer intervals, depending upon the particular needs of the process.

Although in a given process, it may be desirable to flow microcapsules at a relatively stable frequency, in a number of aspects, the frequency for the flowing microcapsules can differ depending upon the desired applications, the nature of the fluids being flowed, and the like. In general, however, microcapsules being flowed into a partitioning or droplet generating junction are flowed at greater than 50 Hz, greater than 100 Hz, greater than 250 Hz, greater than 500 Hz, greater than 750 Hz, greater than 1000 Hz, greater than 1500 Hz, greater than 2000 Hz, or even greater than 5000 Hz or even 10,000 Hz, while still achieving the desired occupancy and other process goals. In certain cases, these flow frequencies may be maintained after the partitioning junction, such that partitioned microcapsules are flowing out of the droplet generation junction at frequencies of at least or greater than 50 Hz, at least or greater than 100 Hz, at least or greater than 500 Hz, at least or greater than 750 Hz, at least or greater than 1000 Hz, at least or greater than 1500 Hz, at least or greater than 2000 Hz, or even at least or greater than 5000 Hz or 10,000 Hz.

Figure 6A:
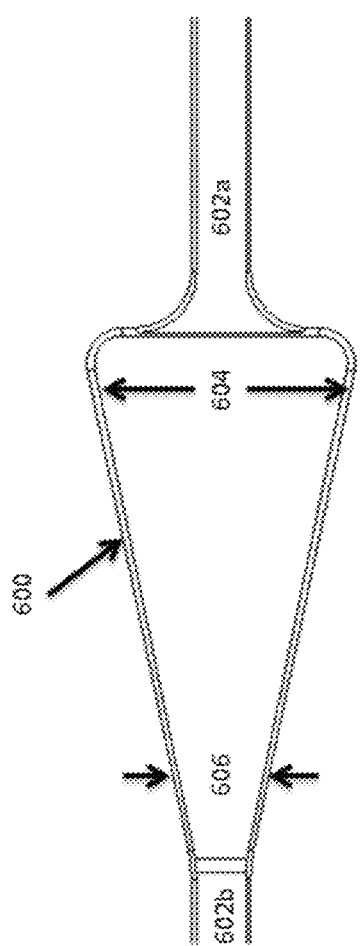
FIGS. 6A and 6B illustrates an example microcapsule flow regulating structure.
Figure 6B:
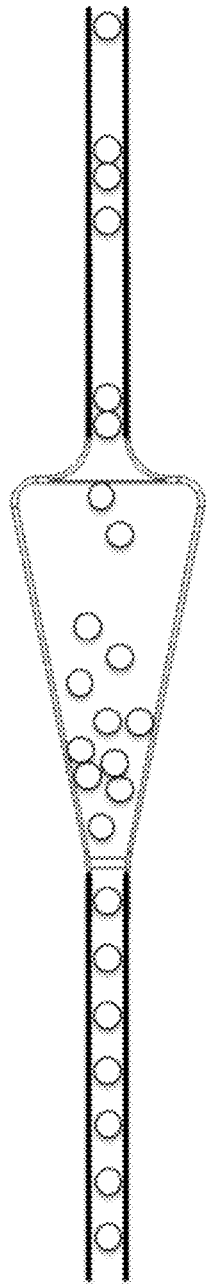

A number of approaches may be adopted to regulate bead flows within the microfluidic channel segments of the devices described herein. For example, in some cases, these regulators include "gathering zones" in which the microcapsules will flow into and gather before flowing out of the gathering zone. These zones are configured to more effectively meter the flow of the microcapsules through the inclusion of funneling structures or channel profiles to better meter the flow of individual microcapsules. Examples of such structures are alluded to above, and are shown in FIGS. 4 and 6B. A first example includes the channel interface shown as funneling zone 452 integrated within the interface of channel segment 402 and reservoir 430.

In a similar fashion, a microcapsule flow regulator may be integrated within the channel segment itself, e.g., channel segment 402 in FIG. 4, rather than at the interface with the reservoir, e.g., reservoir 430 of FIG. 4. An example of this structure includes the flow regulator structure 600 illustrated in FIG. 6A. As will be appreciated, the microcapsule flow regulating structure 460 may also function as a passive fluid valve during filling of the device, e.g., valve 436, as described with respect to channel segments 402, 404 and 406, above. As with funneling structure 452, flow regulator 600 includes a broadened region of channel segment 602 (shown at the interface as channel 602a) at region 604 that narrows at region 606 until it rejoins the cross-sectional dimensions of the outlet portion of channel segment 602 (shown at the interface as segment 602b). As the microcapsules entered the expanded region 602, the convective flow will allow multiple microcapsules to gather or aggregate within the overall gathering region. Once sufficient numbers of microcapsules have aggregated, they will begin to flow out through the narrowed region into channel segment 604 in a metered and more controlled manner. This is schematically illustrated in FIG. 6B, showing microcapsules flowing at irregular frequency into the microcapsule flow regulating structure, and flowing out of the regulator at a more regular frequency. As will be appreciated, a channel network may include one or more flow regulators arranged in series or in parallel within a given flow path, e.g., the fluid connection between two points in the overall network. While these flow regulators may include those having the shape and configuration as shown in FIGS. 6A and 6B, they may also include different shapes and configurations. For example, the broadened regions of the flow regulator may include triangular shapes similar to that shown in FIGS. 6A and 6B, or may include elongated triangular shapes. Likewise, the broadened region of the flow regulators may include circular, elliptical or semi-circular or semi-elliptical shapes, or may include a tapered funnel shape like the channel interfaces described elsewhere herein. As will be appreciated, the basic structural components of these exemplary flow regulators is a broadened channel region at the point a flow enters into the regulator, with a tapered, narrowing or funneling portion as the flow enters into the subsequent channel or channel network. These broadened regions will typically have wider cross sections that are from 1.1× to 20× the cross section of channel segments flowing into the broadened region. In some aspects, these broadened regions are anywhere from 2× to 10× the cross-section of the entering channel segment (as compared against the same cross-sectional measurement, e.g., width to width, depth to depth, etc.), and in some cases, from 2× to 5× the cross section of the entering channel segment. In some cases, more than one cross-sectional dimension may be varied over the inlet channel, e.g., both width and depth may be different. Further, although in some aspects, where both dimensions are varied, they will be greater than those of the inlet channel, in some cases, provided at least one of width and depth is increased, the other dimension may be decreased, depending upon the desired flow characteristics through the flow regulator.

In other examples, multiple microcapsule containing channels are brought together at a gathering zone to bring in a higher number of microcapsules into the junction and its connected effluent channel segment. This allows voids in the flow of microcapsules in one channel to be filled by microcapsules flowing in from the other channel(s). These channel segments may include separate channel segments provided within the channel network as a gathering zone, or as noted above, they may comprise multiple inlet channel segments that are fluidly connected to a microcapsule containing reservoir. Further, as noted previously, these channel segments may deliver microcapsules from a single source or population of microcapsules to the same channel segment, or they may deliver microcapsules from different sources, e.g., reservoirs, to a common channel segment, where such different microcapsules include different reagents.

As noted above, the microfluidic devices and systems of the present disclosure may include improved interface components useful in operation of the devices and systems, and interface components that may be particularly useful in the handling and manipulation of microcapsule compositions and partitioned compositions.

Examples of interfaces useful for microcapsule and partition manipulation include those useful for one or both of deposition and harvesting of such compositions to and from such devices. For example, as noted previously, movement and transport of microcapsules in solution can be subject to some variability. This variability can, in some instances, carry over to transport of these solutions from the systems in which they are created into other systems and/or vessels, e.g., storage vessels such as tubes, wells, vials, or the like, or in transporting them from storage vessels, e.g., tubes, wells, vials or the like, into systems for their subsequent processing, e.g., microfluidic partitioning systems like those described above. In one example, a microcapsule solution or suspension is provided within a storage vessel that includes a pierceable wall or base surface. Corresponding piercing structures may be provided within a reservoir on a fluidic device. By inserting the storage vessel into the reservoir, the pierceable wall is penetrated by the piercing structures to release the microcapsule suspension into the reservoir.

An example of this type of interface is schematically illustrated in FIGS. 7A and 7B. As shown in FIG. 7A, a storage vessel, such as tube 702 is provided for holding fluid reagents, such as a microcapsule suspension 704, as described elsewhere herein. A surface of the vessel, e.g., base surface 706 is provided as a pierceable layer. Pierceable layers may be provided in any of a variety of different configurations. For example, they may simply include walls of the same material as the rest of the vessel, but which are sufficiently thin to allow piercing. Such walls may be thinner than other walls in the vessel. Alternatively, the pierceable surfaces may include different materials from that of the remainder of the vessel, such as a pierceable septum (e.g., nitrocellulose, PVDF, latex, or any other similarly used materials), a foil surface, or any of a number of other pierceable membranes. Likewise, a surface of the storage vessel may be provided with a valving structure that may be active or passive. In many cases, passive valves, such as pressure triggered check valves may be employed in base surface 706 of the storage vessel.

In use, the storage vessel is mated with the reservoir 708 in a device 710, as shown in FIG. 7B. Reservoir 708 is configured with piercing structures 712 that are positioned to contact and penetrate the base surface 706 of the storage vessel when the vessel is inserted into the reservoir 708. Once inserted, the base surface 706 is ruptured and the microcapsule suspension 704 contained in vessel 702 is permitted to drain into reservoir 708. In some cases, vessel 702 may be provided with additional components to facilitate driving of the suspension into the reservoir, such as a plunger or other pressurizing device, to force the suspension from the vessel. In other cases, simple gravity flow may be used to transfer the suspension. In some cases, the piercing structure and wall or base component of the vessel maybe configured to optimize the transfer of the suspension from the vessel to the reservoir, through the inclusion of hydrophobic interior coatings on the vessel, flash-mitigating piercing structures (e.g., to reduce the possibility that remnants of the pierced surface may block flow of the suspension out of the vessel). In alternate aspects, dissolvable, degradable or otherwise activatable barriers may be provided in order to allow for the controlled dispensing of the suspension. Such barriers include, e.g., dissolvable films or membranes that are degraded, dissolved or rendered sufficiently permeable to dispense the suspension upon application of a stimulus. Such barriers may be degraded upon application of a specific chemical, thermal, electromagnetic, or other stimulus.

Similar to the interfaces described above, in some cases for harvesting either microcapsules or partitioned microcapsules or other materials from devices, such interface components may include, e.g., a pierceable base layer for the harvesting reservoir, e.g., reservoir 216 shown in FIG. 2, or reservoir 438 of the device illustrated in FIG. 4, to allow access to and removal of partitioned microcapsules from the terminal reservoir without necessarily removing the interfaced vacuum source. In operation, at the conclusion of a partitioning operation, the base of the terminal reservoir may be pierced, and the generated partitions are either removed or allowed to drain or flow into a waiting receptacle, e.g., by reversing the vacuum source to apply pressure to the reservoir 438, to drive the partitioned microcapsules through the pierced base layer of the reservoir, or through gravity driven flow. This waiting receptacle may be integrated into the device, or positioned adjacent to the microfluidic device in order to receive the partitioned microcapsules.

In other examples, one or both of the reservoir and storage vessel may be configured to provide efficient transfer from one to the other. For example, in some cases, a vessel including a microcapsule suspension may be provided with an interface component that allows it to be mated, connected and/or coupled directly to the receiving reservoir to efficiently transfer its contents. In some cases, the connection may be bounded by a check valve to prevent movement of the suspension until an appropriate driving force is applied to the suspension.

In addition to fluidic interfaces, the devices and systems described herein may also include one or more of a variety of mechanical or physical interface components. Such components include, for example, handling components to facilitate the manual or automated movement and handling of the devices, alignment components, to ensure proper placement and alignment of the devices on instruments, holders and the like, as well as functional components, to allow for additional manipulation of sample materials within the devices. Examples of handling components include tabs, walls, or other surfaces that are positioned away from critical or sensitive surfaces of a device (e.g., optical windows, surfaces prone to contamination, etc.), as well as surfaces that are configured to facilitate handling, whether manual or automated, e.g., with sufficient size and/or textured surfaces to ensure grip and control.

Examples of alignment structures include mechanical elements that ensure alignment of a device with a corresponding instrument, or other fixture, such as beveled corners, device shapes, and integrated key elements (e.g., tabs, slots, posts, or the like) that mate with complementary structures on the other fixture. Such alignment components also include optically detected components, such as registration marks or fiducials, barcode tags, or other machine readable components integrated into or attached to a device.

A wide variety of functional components or functional component interfaces are also envisioned, including, e.g., those interface components that are important for operation of the device. Examples of such interface components include, for example, gasket structures that may be integrated into or separately placed over the upper surfaces of one or more reservoirs, to ensure sealed application of pressures or vacuums to the devices described herein. In certain aspects, these gaskets will be either integrated into the device, or provided as a separate, disposable component, rather than being integrated into an instrument, in order to minimize the possibility of instrument contamination. Other examples of functional interface components include interfaces for mixing or agitating components within the reservoirs. Such components are useful in come cases to prevent settling of microcapsule compositions. These interfaces may comprise actual agitation components, such as piezoelectric, acoustic, or mechanical vibration components integrated into the devices, or they may comprise surfaces that are suitable for or are configured to interface these components on a corresponding instrument system or other fixture.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. For example, particle delivery can be practiced with array well sizing methods as described. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. A method for partitioning microcapsules, comprising:
(a) providing a microfluidic device comprising a microfluidic channel network, wherein the microfluidic channel network comprises (i) a droplet generation junction, (ii) a first channel segment fluidly connecting a source of microcapsules to the droplet generation junction, (iii) a second channel segment fluidly connecting a source of partitioning fluid to the droplet generation junction, and (iv) a third channel segment fluidly connected to the droplet generation junction and providing an outlet to the droplet generation junction; and (b) flowing (i) an aqueous fluid comprising a suspension of microcapsules from the source of microcapsules along the first channel segment and (ii) a partitioning fluid from the source of partitioning fluid along the second channel segment into the droplet generation junction to form a population of droplets of the aqueous fluid in the partitioning fluid, wherein the population of droplets flow along the third channel segment, and wherein (1) the first channel segment has a cross-sectional dimension that provides a flow rate of the aqueous fluid or (2) the second channel segment has a cross-sectional dimension that provides a flow rate of the partitioning fluid, such that greater than 50% of droplets of the population of droplets are occupied by microcapsules from the suspension of microcapsules.

2. The method of claim 1, wherein the flow rate of the aqueous fluid or the partitioning fluid is such that greater than 75% of droplets of the population of droplets are occupied by microcapsules from the suspension of microcapsules.

3. The method of claim 2, wherein the flow rate of the aqueous fluid or the partitioning fluid is such that greater than 90% of the droplets of the population of droplets are occupied by microcapsules from the suspension of microcapsules.

4. The method of claim 1, wherein fewer than 25% of droplets of the population of droplets comprise more than one microcapsule.

5. The method of claim 4, wherein fewer than 20% of droplets of the population of droplets comprise more than one microcapsule.

6. The method of claim 5, wherein fewer than 15% of droplets of the population of droplets comprise more than one microcapsule.

7. The method of claim 6, wherein fewer than 10% of droplets of the population of droplets comprise more than one microcapsule.

8. The method of claim 7, wherein fewer than 5% of droplets of the population of droplets comprise more than one microcapsule.

9. The method of claim 1, wherein at least 80% of droplets of the population of droplets comprise a single microcapsule.

10. The method of claim 9, wherein at least 90% of droplets of the population of droplets comprise a single microcapsule.

11. The method of claim 10, wherein at least 95% of droplets of the population of droplets comprise a single microcapsule.

12. The method of claim 1, wherein (b) comprises providing one or more pressure differentials across the first and second channel segments to provide the flow rate of the aqueous fluid or the partitioning fluid.

13. The method of claim 1, wherein the microfluidic channel network further comprises one or more flow controlling structures within the first channel segment that provide the flow rate of the aqueous fluid.

14. The method of claim 1, wherein the suspension of microcapsules is a suspension of beads.

15. The method of claim 1, wherein the suspension of microcapsules is a suspension of gel microcapsules.

16. The method of claim 1, wherein a given microcapsule of the suspension of microcapsules comprises a barcode sequence.

17. The method of claim 16, wherein the barcode sequence is covalently linked to the given microcapsule.

18. The method of claim 1, wherein a given microcapsule of the suspension of microcapsules comprises a labile linkage.

19. The method of claim 18, wherein the labile linkage is a chemically cleavable linkage.

20. The method of claim 19, wherein the chemically cleavable linkage is a disulfide linkage.

21. The method of claim 1, wherein a given microcapsule of the suspension of microcapsules comprises a cross-linked polymer network.

22. The method of claim 1, wherein the aqueous fluid further comprises a reducing agent.

23. The method of claim 1, wherein the first and second channel segments have cross-sectional dimensions that provide the flow rate of the aqueous fluid and the flow rate of the partitioning fluid such that greater than 50% of droplets of the population of droplets are occupied by microcapsules from the suspension of microcapsules.

24. The method of claim 1, wherein the flow rate of the aqueous fluid or the flow rate of the partitioning fluid is such that some of the droplets of the population of droplets are unoccupied by microcapsules from the suspension of microcapsules.

25. The method of claim 24, wherein the flow rate of the aqueous fluid and the flow rate of the partitioning fluid are such that some of the droplets of the population of droplets are unoccupied by microcapsules from the suspension of microcapsules.

* * * * *